US009939356B2

(12) United States Patent
Cremins

(10) Patent No.: US 9,939,356 B2
(45) Date of Patent: *Apr. 10, 2018

(54) METHOD AND COMPOSITION FOR STAINING AND PROCESSING A URINE SAMPLE

(71) Applicant: IRIS International, Inc., Chatsworth, CA (US)

(72) Inventor: Jack Cremins, Waterbury, CT (US)

(73) Assignee: Iris International, Inc., Chatsworth, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/137,749

(22) Filed: Apr. 25, 2016

(65) Prior Publication Data

US 2016/0238496 A1 Aug. 18, 2016

Related U.S. Application Data

(63) Continuation of application No. 14/216,562, filed on Mar. 17, 2014, now Pat. No. 9,322,753.

(60) Provisional application No. 61/799,014, filed on Mar. 15, 2013.

(51) Int. Cl.
| | | |
|---|---|---|
| *G01N 1/30* | (2006.01) | |
| *G01N 33/50* | (2006.01) | |
| *G01N 15/14* | (2006.01) | |
| *G01N 15/06* | (2006.01) | |
| *G01N 15/00* | (2006.01) | |
| *G01N 15/10* | (2006.01) | |

(52) U.S. Cl.
CPC ............... *G01N 1/30* (2013.01); *G01N 15/06* (2013.01); *G01N 15/1459* (2013.01); *G01N 15/1463* (2013.01); *G01N 33/50* (2013.01); *G01N 2001/302* (2013.01); *G01N 2015/0046* (2013.01); *G01N 2015/1006* (2013.01); *G01N 2015/1497* (2013.01)

(58) Field of Classification Search
CPC ..................................................... A61K 38/44
See application file for complete search history.

(56) References Cited

U.S. PATENT DOCUMENTS

| | | |
|---|---|---|
| 3,894,845 A | 7/1975 | McDonald |
| 3,988,209 A | 10/1976 | McDonald |
| 4,473,530 A | 9/1984 | Villa-Real |
| 4,612,614 A | 9/1986 | Deindoerfer et al. |
| 4,622,298 A | 11/1986 | Mansour et al. |
| 4,973,450 A | 11/1990 | Schluter |
| 5,132,232 A | 7/1992 | Parker |
| 5,985,247 A | 11/1999 | Soetanto |
| 6,632,676 B1 | 10/2003 | Crews et al. |
| 9,322,753 B2 | 4/2016 | Cremins |
| 2007/0292346 A1 | 12/2007 | Fan et al. |
| 2010/0087726 A1 | 4/2010 | Ruff et al. |
| 2012/0322099 A1 | 12/2012 | Lapen et al. |
| 2012/0329050 A1 | 12/2012 | Nadeau et al. |

FOREIGN PATENT DOCUMENTS

| | | |
|---|---|---|
| CN | 1610752 A | 4/2005 |
| CN | 101490547 A | 7/2009 |
| CN | 101711670 A | 5/2010 |
| JP | 2010-151566 | 7/2010 |
| JP | 2010-213598 | 9/2010 |
| WO | 03-035895 | 5/2003 |
| WO | 2005-095454 | 10/2005 |
| WO | 2008-010760 | 1/2008 |
| WO | 2011-087789 | 4/2011 |
| WO | 2012-055069 | 5/2012 |

OTHER PUBLICATIONS

Chukwu et al. African J of Microbiology Research, 2011, 5(21):3351-3356.*
Vladutiu, Bioscience Reports, 1984, 4:1079-1088.*

* cited by examiner

*Primary Examiner* — Bin Shen
(74) *Attorney, Agent, or Firm* — Kilpatrick Townsend & Stockton LLP

(57) ABSTRACT

The present disclosure relates to a staining methodology employing a particle contrast agent composition capable of rapidly staining cells in a single step. The particle contrast agent composition can be comprised of a combination of one or more particle contrast agents and one or more permeabilizing agents, optionally including one or more fixing agents and other components. The particle contrast agent composition can include Crystal Violet, 5PD-Lytic, and Proclin 300.

20 Claims, 15 Drawing Sheets

METHOD AND COMPOSITION FOR STAINING AND PROCESSING A URINE SAMPLE

CROSS REFERENCE TO RELATED APPLICATIONS

The present application is a continuation of U.S. patent application Ser. No. 14/216,562, filed Mar. 17, 2014, titled "Method and Composition for Staining and Processing a Urine Sample," (now U.S. Pat. No. 9,322,753, issued Apr. 26, 2016), which claims the benefit of U.S. Patent Application No. 61/799,014 filed Mar. 15, 2013, entitled "Analysis of Particles in Urine Samples," which are hereby incorporated by reference in their entirety.

TECHNICAL FIELD

The present disclosure relates to particle contrast agents generally and more specifically to particle contrast agent compositions for use in wholly or partially automated devices to discriminate and quantify particles in fluid samples, such as urine samples.

BACKGROUND

Urine sediment analysis is one of the most commonly performed diagnostic tests for providing an overview of a patient's health status. A urine sample can be obtained from a patient's body and stored in a test tube for later processing and analysis. The appearance of certain characteristic sediments also called formed elements in a urine sample may be clinically significant and/or be indicative of pathological conditions in a subject.

Generally, abnormal urine may contain a variety of formed elements, such as blood cells, epithelial cells, crystals, casts, or microorganisms. For example, urine samples may contain cells of hematological origin. Erythrocytes or red blood cells (RBCs) may be present in the urine as a result of bleeding (hematuria) at any point in the urogenital system from the glomerulus to the urethra. The presence of leukocytes or WBCs, neutrophils, eosinophils may have clinical significance. Glitter cells are a type of neutrophil seen in hypotonic urine of specific gravity 1.010 or less. The presence of lymphocytes has been used as an early indicator of renal rejection after transplant. Eosinophils are associated with drug-induced interstitial nephritis, Mucus threads originating from the kidney or the lower urinary tract can be present.

Urine samples may also contain cells of epithelial origin. A few renal epithelial cells also called renal tubular cells, may be found in the urine of healthy persons because of normal exfoliation. However, the presence of excessive renal tubular cells is indicative of active renal disease or tubular injury. Of the various types of epithelial cells found in urine (renal, transitional or urothelial, and squamous), renal epithelial cells are the most significant clinically. They are associated with acute tubular necrosis, viral infections (such as cytomegalovirus), and renal transplant rejection. Their presence is also increased with fever, chemical toxins, drugs (especially aspirin), heavy metals, inflammation, infection, and neoplasms. Moreover, the presence of inclusion bodies may be seen in viral infections, such as rubella and herpes, and especially with cytomegalovirus.

Urine can also contain transitional epithelial cells or urothelial cells. Transitional epithelial cells are the multilayer of epithelial cells that line the urinary tract from the renal pelvis to the distal part of the male urethra and to the base of the bladder (trigone) in females. They may be difficult to distinguish from renal epithelial cells, but they are generally larger and more spherical. A few transitional cells are present in the urine of healthy persons. Increased numbers are associated with infection. Large clumps or sheets of these cells may be seen with transitional cell carcinoma.

Urine can also contain squamous epithelial cells. Squamous epithelial cells line the urethra in females and the distal portion of the male urethra. The presence of large numbers of squamous cells in females generally indicates vaginal contamination.

Urine can also contain clue cells. Clue cells are another type of squamous cell of vaginal origin, may be seen contaminating the urine sediment. This squamous epithelial cell is covered or encrusted with a bacterium, *Gardnerella vaginalis*, whose presence is indicative of a bacterial vaginitis.

Urine can also contain oval fat bodies, renal tubular fat, or renal tubular fat bodies. These bodies are renal epithelial cells (or macrophages) that have filled with fat or lipid droplets. The fat may be either neutral fat (triglyceride) or cholesterol; they have the same significance clinically. Presence of oval fat bodies in urine is indicative of disease abnormality and should not be overlooked. They are often seen with fatty casts and fat droplets in the urine sediment and are associated with massive proteinuria as seen in nephrotic syndrome.

Urine can also contain microorganisms such as bacteria and yeast. Normally, urine is sterile, or free of bacteria. However, certain bacteria are typically seen in urine of an alkaline pH. Associated sediment findings may include the presence of WBCs (neutrophils) and casts (WBC, cellular, granular, or bacterial). Although infections are most often due to gram-negative rods of enteric origin, infectious organisms may also be gram-positive cocci.

In addition, yeast may be seen in urine, especially as the result of vaginal contamination such as contamination from female patients with yeast infections. It is also associated with diabetes mellitus owing to the presence of urinary glucose. Yeast is a common contaminant, from skin and the environment, and infections are a problem in debilitated and immunosuppressed or immunocompromised patients.

Traditionally, analysis of sediments in urine has been performed by visual inspection using a microscope in a general laboratory. With these approaches, a urine sample is first subjected to centrifugal separation and enriched. Sediments thus obtained are in some cases stained and then loaded on a microscope slide, and are subjected to manual determination and counting under the microscope.

Sample preparation steps can include concentration of the urine sediments by centrifugation and sometimes application of a microscopy stain to enhance contrast, e.g., between sediment types such as RBCs, WBCs, and epithelial cells. In a manual count, the technician views the wet mount slide, distinguishing among types of visible cells or by their appearance using professional judgment, and manually counts the number of observed urine sediment of different types within a predetermined area.

Various stains have been used to stain cells or cellular structures found in urine samples. For example, Wright's stain is a stain that has been used to stain urine samples for examination under a light microscope. Staining a urine sample involves the use of multiple solutions and steps in proper order to ensure the staining agent is correctly applied and the cell structure is appropriately preserved. A fixing agent can be applied to the sample in a first step to preserve the sample from degredation and maintain the cell structure. Afterwards, a permeabilizing agent can be applied to the sample in a second step to dissolve cell membranes in order to allow the staining agent to enter the cells. The staining agent can be applied to the sample in a third step to stain the appropriate structures. The sample may be further rinsed for observation, or additional steps may be taken to apply additional stains, counterstains, or other perform other actions.

It is important to perform the steps in the appropriate order for the appropriate amounts of time. If the sample is permeabilized before being fixed, the cell structures in the sample can be degraded prior to being fixed and any ability to discern the original cellular morphology is lost. Additionally, the staining cannot occur prior to the permeabilizing step, or the staining agent will not properly penetrate the cells and stain the structures within the cells. Additionally, if any of the steps, such as fixing, permeabilizing, and staining, are performed too rapidly, the cell's morphology may be lost and/or the cell and its internal structures may not be properly stained. Also, the use of pH modifiers may be necessary prior to other steps in order to ensure proper functionality of components that cannot function properly in the urine natural pH. Current staining techniques require multiple steps and significant time.

Current staining techniques require dilution of samples in the contrast agents generally around 9 parts contrast agent to 1 part sample. It can be undesirable to have large-volume mixtures for use with image-based analysis systems such as flow cytometery systems, at least because of the time it takes to process a volume of a mixture.

Automated analyzers are becoming more prevalent. The use of systems for urine analysis is generally described in U.S. Pat. No. 4,473,530 to Villa-Real, entitled "Compact Sanitary Urinalysis Unit"; U.S. Pat. No. 3,894,845, entitled "Urine Collection and Analysis Device" and U.S. Pat. No. 3,988,209, entitled "Microorganism Analysis Device", both to McDonald; U.S. Pat. No. 4,973,450 to Schluter, entitled "Device for Urinalysis"; U.S. Pat. No. 4,622,298 to Mansour, et al., entitled "Detection and Quantitation of Microorganisms, Leukocytes and Squamous Epithelial Cells in Urine"; and U.S. Pat. No. 5,132,232 to Parker, entitled "Method and Apparatus for Preparation of Liquids for Examination." U.S. Pat. No. 4,612,614 to Deindoerfer, et al., entitled "Method of Analyzing Particles in a Fluid Sample", reports a method for analyzing urinary sediments by distributing a sample over an extended area, such as a microscope slide or a flow cell. Deindoerfer, et al. reports the use of a plurality of optical still images of the sample that are converted into electronic images which are displayed in an array ordered by classes of visually discernable characteristics. However, many of these earlier developed urine analysis systems generally lacked the throughput, the accuracy, and/or the general applicability required for adaptation across all targets/subjects for all intended purposes.

For automation of urinary sediment determination, an automated flow microscope may be used (e.g., flow-type automatic microscope—iQ® 200, Iris Diagnostics). With these types of devices, a urine sample is introduced to a flat type flow cell without pre-concentration and images are taken and stored while the sample is flowing through the flow cell. However, urinary sediments are diversified in their morphology and many sediments are being damaged, and therefore, determination of images taken with good accuracy are difficult to achieve. It is particularly difficult to determine small-sized sediments, such as erythrocytes (especially dysmorphic erythrocytes), bacteria and crystals with good accuracy without external user validation.

The various automated systems described above rely on rapid analysis of samples. The number of and duration of the steps of the staining process can be a limiting factor in the speed and efficacy of automated particle analysis systems. Automated particle analysis systems can be more efficient if the staining process is shortened, and further more efficient if the staining process is performed in a single step. Additionally, the automated particle analysis systems can be more efficient if the total size of the sample is kept to a minimum.

SUMMARY

A particle contrast agent composition is disclosed for staining particles of a urological fluid sample for imaging in an automated particle analysis system. The particel contrast agent composition can include Crystal Violet present in amounts sufficient to result in concentrations between 50 µM and 500 µM under staining conditions. The particle contrast agent composition can further include a permeabilizing agent selected from the group consisting of 5 PD Lytic and saponin.

In an embodiment, the permeabilizing agent can be 5 PD Lytic present in amounts sufficient to result in concentrations of about 3.5% by weight under staining conditions. In an embodiment, the Crystal Violet can be present in amounts sufficient to result in concentrations of about 86 µM under staining conditions. In an embodiment, the particle contrast agent composition can further include a phosphate buffered saline including at least sodium phosphate dibasic and potassium phosphate monobasic.

In an embodiment, the particle contrast agent composition can include an antimicrobial agent. In some embodiments, the antimicrobial agent can be Proclin 300 and the particle contrast agent composition can also include 80% pure or greater Crystal Violet present in amounts sufficient to result in concentrations of about 86 µM under staining conditions. In some embodiments, the particle contrast agent composition can also include sodium chloride and a phosphate buffered saline including at least sodium phosphate dibasic and potassium phosphate monobasic.

A method is disclosed for treating particles of a urological fluid sample for imaging using in an automated particle analysis system. The method can include combining a particle contrast agent composition and the urological fluid sample into a sample mixture resulting in a final concentration of the particle contrast agent composition by weight of the sample mixture between about 1% and about 20%. The method can further include incubating the sample mixture at a temperature above 20° Celsius for fewer than 90 seconds. In some embodiments, the particle contrast agent composition includes Crystal Violet present in amounts sufficient to result in concentrations between 50 µM and 500 µM under staining conditions and 5PD-Lytic.

In some embodiments, the 5PD-Lytic can be present in amounts sufficient to result in concentrations of about 3.5% by weight under staining conditions. The Crystal Violet can be present in amounts sufficient to result in concentrations of about 86 µM under staining conditions. The final concentration of particle contrast agent composition by weight of the sample mixture can be between about 10% and about 20%. The sample mixture can be incubated at between 30° C. and 50° C. for fewer than 60 seconds.

In some embodiments, the final concentration of particle contrast agent composition by weight of the sample mixture is about 15% and the the sample mixture is incubated at between 30° C. and 50° C. for fewer than 60 seconds.

In some embodiments, the sample mixture is incubated at between 40° C. and 50° C. for between 30 and 35 seconds. The Crystal Violet can be approximately 80% pure or greater. In some embodiments, the particle contrast agent composition further includes Proclin 300.

In some embodiments, the particle contrast agent composition further comprises adding sodium chloride and a phosphate buffered saline including at least sodium phosphate dibasic and potassium phosphate monobasic.

The above described and many other features and attendant advantages of embodiments of the present invention will become apparent and further understood by reference to the following detailed description when considered in conjunction with the accompanying drawings.

BRIEF DESCRIPTION OF THE DRAWINGS

The specification makes reference to the following appended figures, in which use of like reference numerals in different figures is intended to illustrate like or analogous components

DETAILED DESCRIPTION

Figure 1:
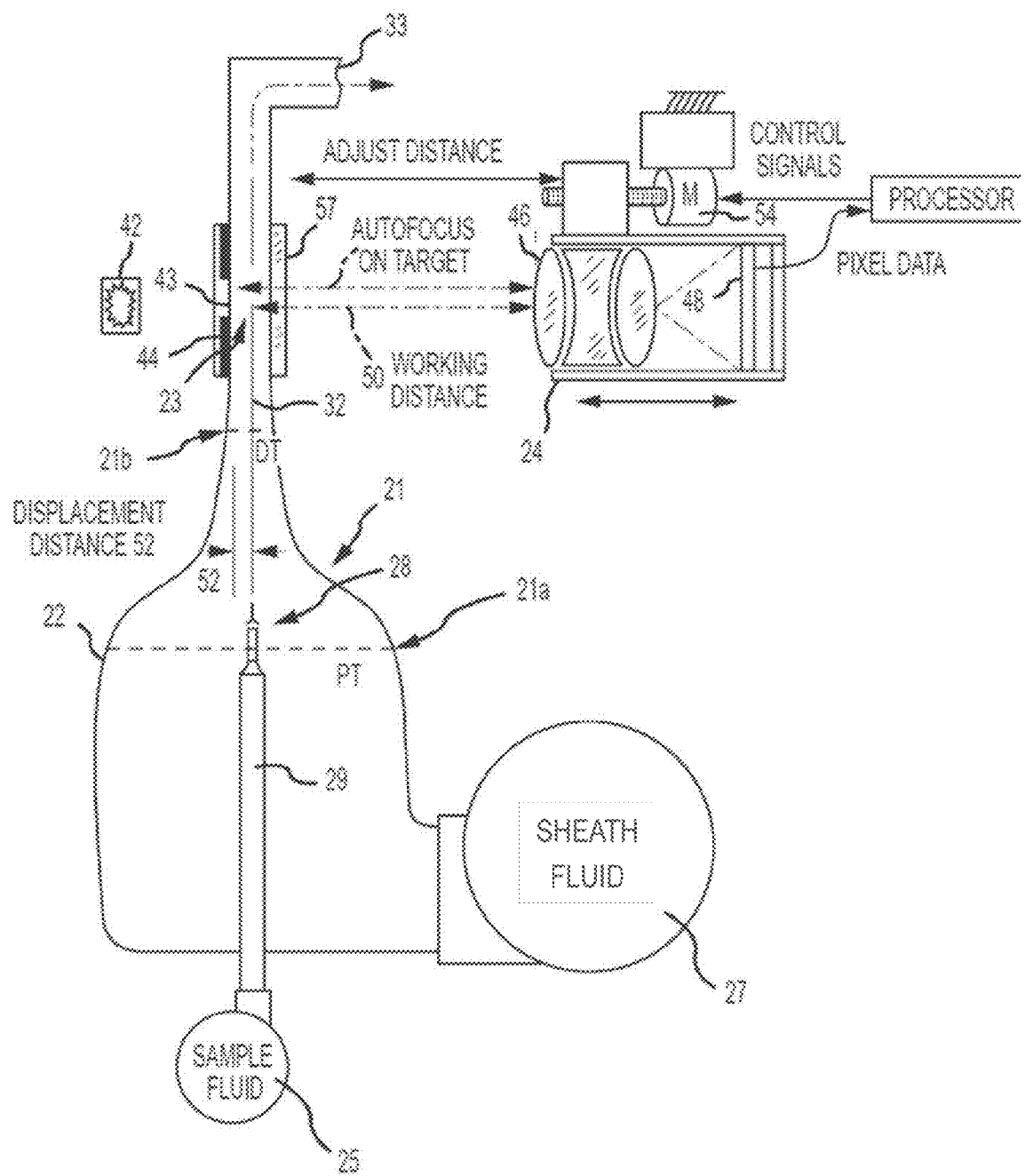
FIG. 1 is a schematic diagram of a flowcell for conveying a sample fluid according to one embodiment.

The present disclosure relates to a surprising and unexpected particle contrast agent composition for rapidly generating visual distinctions in a fluid sample, such as a urine sample. The particle contrast agent composition can be especially useful in automated flow cytometry systems. The particle contrast agent composition is comprised of a combination of a particle contrast agent and a permeabilizing agent. The particle contrast agent composition can include a fixing agent and/or an antimicrobial agent. In one embodiments, the particle contrast agent composition is a mixture of Crystal Violet, Saponin, and Proclin 300. In an embodiment that is surprisingly effective, under staining conditions, the Crystal Violet is present in amounts sufficient to result in concentrations of about 0.57 mM, the Saponin is present in amounts sufficient to result in concentrations of approximately 23.3% by weight, and the Proclin 300 is present in amounts sufficient to result in concentrations of approximately 0.05% by weight, with deionized water at about 76.7% by weight.

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative embodiments but, like the illustrative embodiments, should not be used to limit the present disclosure. The elements included in the illustrations herein may be drawn not to scale.

Prior to the embodiments described herein, there was no published protocol that allows for the development and the methods of use of particle contrast agent compositions for performing particle/cellular differential categorization and subcategorization in urine samples for image-based analysis while maintaining viable or substantially intact cells, with the option of staining and permeabilizing steps occurring while in flow, to achieve white cell, epithelial cells, bacteria staining, that enhance differential visualization.

Aspects and embodiments of the present disclosure are based on the surprising and unexpected discovery that certain particle contrast agent compositions, including for example, stain/dye compositions, and/or combinations thereof, have unexpected properties and efficacy when used to perform automated, image-based sample analysis, such as urine sediment sample analysis.

Urinalysis—Particle Analysis System

The compositions and method disclosed herein can be used with many different types of urine analysis imaging systems, such as the IQ Urine Analysis sold by Iris International. In particular, the compositions and methods described herein can be used with image-based sample analysis, such as flowcell analysis. An example of such a flowcell analysis can include traditional, known methods of flow cytometry. Additionally, the compositions and methods described herein can be advantageously used with the flowcell analysis systems and methods described in brief detail below and described further in the co-filed application entitled "Flowcell, Sheath Fluid, and Autofocus Systems and Methods For Particle Analysis In Urine Samples", application Ser. No. 14/217,228, filed Mar. 17, 2014, which is hereby incorporated by reference.

FIG. 1 is a schematic representation of an exemplary flowcell 22 for conveying a sample fluid (e.g., a sample mixture, as described in further detail below) through a viewing zone 23 of a high optical resolution imaging in a configuration for imaging microscopic particles in a sample flow stream 32 using digital image processing. Flowcell 22 is coupled to a source 25 of sample fluid which may have been subjected to processing, such as contact with a particle contrast agent composition and heating.

Flowcell 22 may also be coupled to a sheath fluid source 27 to aid the flow of the sample. In one embodiment, the sheath fluid is an aqueous salt solution having a pH around 7.0 and a specific gravity of 1.007 at 20° C., which can be obtained from IRIS International, Inc. under the trade name LAMINA.

The sample fluid is injected through a flattened opening at a distal end 28 of a sample feed tube 29, and into the interior of the flowcell 22 at a point where the sheath fluid flow has been substantially established resulting in a stable and symmetric laminar flow of the sheath fluid above and below (or on opposing sides of) the ribbon-shaped sample stream. The sample sheath fluid may be supplied by precision metering pumps that move the sheath fluid with the injected sample fluid along a flowpath that narrows substantially. In one embodiment, the sheath fluid envelopes and compresses the sample fluid in the zone 21 where the flowpath narrows. Hence, the decrease in flowpath thickness at zone 21 can contribute to a geometric focusing of the sample stream 32. The sample fluid ribbon 32 is carried along with the sheath fluid downstream of the narrowing zone 21, passing in front of, or otherwise through the viewing zone 23 of, the high optical resolution imaging device 24 where images are collected, for example, using a CCD. The sample fluid ribbon flows together with the sheath fluid to a discharge 33.

As shown here, the narrowing zone 21 can have a proximal flowpath portion 21a having a proximal thickness PT and a distal flowpath portion 21b having a distal thickness DT, such that distal thickness DT is less than proximal thickness PT. The sample fluid can therefore be injected through the distal end 28 of sample tube 29 at a location that is distal to the proximal portion 21a and proximal to the distal portion 21b. Hence, the sample fluid can enter the sheath fluid envelope as the sheath fluid stream is compressed by the zone 21.

The digital high optical resolution imaging device 24 with objective lens 46 is directed along an optical axis that intersects the ribbon-shaped sample stream 32. The relative distance between the objective 46 and the flowcell 22 is variable by operation of a motor drive 54, for resolving and collecting a focused digitized image on a photosensor array.

Particle Contrast Agent Composition

Figure 2:
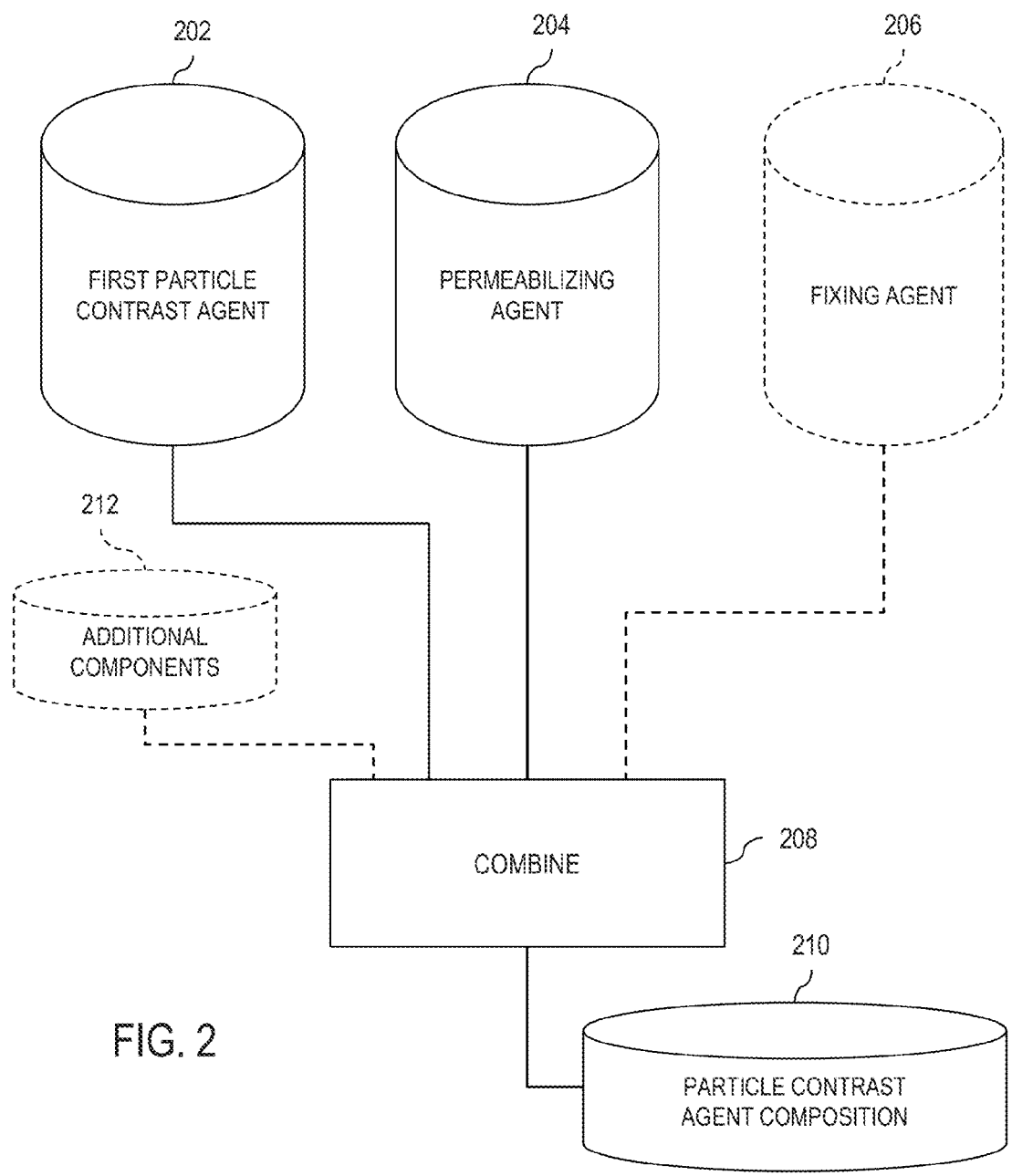
FIG. 2 is a schematic diagram of the preparation of a particle contrast agent composition according to one embodiment.

FIG. 2 is a schematic diagram of the preparation of a particle contrast agent composition according to one embodiment. At block 208, a particle contrast agent 202 and a permeabilizing agent 204 are combined to create the particle contrast agent composition 210. In some embodiments, an optional fixing agent 206 is also combined. The combination at block 208 can be performed in any order and in any suitable way.

In alternate embodiments, additional components 212 are combined at block 208 as part of the particle contrast agent composition 210, as described in further detail below.

The particle contrast agent composition 210 can be provided as part of a kit. The particle contrast agent composition 210 can be provided already prepared or as one or more components that must be combined. The kit may also contain instructions on the use of particle contrast agent composition according to any of the methods described herein and/or instructions for use of any other component of the kit. The kit may also comprise one or more buffers and/or diluents. The kit and or buffer may further comprise at least one of a pH adjusting agent; ionic strength modifier, a surfactant, a chelating agent, sugar, sugar alcohol, protein stabilizers, and/or an antimicrobial agent. In other embodiments, the kit may also comprise a cleaning or flushing solution. The kit may also comprise standards for positive and negative controls, calibrators, or controls. In some embodiments the standard may comprise a standard contain calibrators and/or controls. The kit may also comprise disposable micropipettes, tips or tubes for transferring the components of the kit.

Particle Contrast Agent

The particle contrast agent 202 can be any contrast agent capable of producing visible distinctions in particles in the urine sample. Different contrast agents react or concentrate in different parts of a cell and these properties can be used to advantage to reveal specific parts or areas. Examples of such contrast agents (e.g., stains) include Alcian Blue and Alcian Blue 86 (PAS neutral and acidic mucosubstances); Alizarin Red S; Allura Red AC (azodye red dye#40); Analine Blue (cilia intensified with oxalic acid); Auramine O; Azure B; Azure C; Bismarck Brown; Brilliant Blue FCF (Comassie blue); Brilliant cresyl blue; Brilliant green; Carmium (red nuclear dye composed of Carminic acid and Potassium alum); Congo red; Chlorozol black E (nuclei black, cyto gray, glycogen pink); Cresyl violet acetate; Darrow red; Eosin bluish; Erythrosin B (red dye #3); Ethyl eosin; Fast Green FCF (green dye#3); Fuchin basic—(nuclei and flagella); Fluorescein—(Mercurochrome); Giemsa—peripheral blood smears; Harris hematoxylin—regressive nuclear stain; Indigo Carmine (Blue dye#2); Janus Green B (mitochondria); Jenner Stain—(peripheral blood smears); Light Green SF yellowish; MacNeal—(tetrachrome blood stain); Malachite green; Methyl orange; Martius yellow; Mayer's Hematoxylin—progressive nuclear stain; Methyl violet 2B; Methenamine Silver-Peroidic acid; Methylene violet; May Grunwald—hematological stain; MTT—formazan stain; Mucicarmine-primary tumor stain; Neutral red; Nigrosin; Nile Blue A; Nuclear Fast red C.I. 60760; Napthal AS; Nitro-Blue Tetrazolium—fast formazan dye; Orange G; Orange II; Orcein; Papanicolaou Stain EAS—brilliant cytoplasmic staining; Pararosanilin; Pararosanaline; Periodic Acid Schiff—(PAS, specific carbohydrate stain); Phyloxine B; Protargol S; Pyronin B; Pyronin Y; Resazurin; Romanowsky-Giemsa; Rose Bengal; Safranin O; Sudan Black B; Sudan III—(with alpha-napthol stains myeloid granules); Sudan IV—stains triglycerides; Tartrazine—(azo dye Yellow#5); Thionin—stains meta chromatin; Triphenyl Tetrazolium; TTC—Formazan red dye; Toluidine BlueO; Wright's Stain—(fixative, buffer and stain for conventional blood smears); and Wright Giemsa.

Through non-trivial efforts and experimentation, it has been found that surprisingly effective results can be achieved in the particle contrast agent composition 210, as described in further detail herein, with the use of a particle contrast agent 202 that includes at least one of Crystal Violet, New Methylene Blue, Safranin O, Eosin Y and Methyl Green. The particle contrast agent 202 is added in an amount effective to stain viable and/or substantially intact cells for image-based categorization and subcategorization. The particle contrast agent 202 can be any combination of two or more of the aforementioned particle contrast agents.

The particle contrast agent 202 can be selected to efficaciously obtain discernible stained images of vital and/or substantially intact cells.

In one embodiment, the particle contrast agent 202 includes Crystal Violet. The Crystal Violet can be present in amounts sufficient to achieve between about 50 µM to about 500 µM under staining conditions. As used herein, the term "under staining conditions" refers to when the component is mixed with the sample. The Crystal Violet can be present in amounts sufficient to achieve between about 50 µM to about 500 µM under staining conditions. The Crystal Violet can be present in amounts sufficient to achieve about 320 µM under staining conditions. Surprisingly effective results can be achieved when the Crystal Violet is present in amounts sufficient to achieve about 0.57 mM under staining conditions. Surprisingly effective results can be achieved when the Crystal Violet is present in amounts sufficient to achieve very nearly 0.57 mM under staining conditions. The Crystal Violet can be purified to at least 5% pure. The Crystal Violet can be purified to at least 80%, 81%, 82%, 83%, 84%, 85%, 86%, 87%, 88%, 89%, 90%, 91%, 92%, 93%, 94%, 95%, 96%, 97%, 98%, or 99% pure. The Crystal Violet can be purified to at least 100% pure. The particle contrast agent 202 can be solely Crystal Violet, or can be Crystal Violet combined with one or more additional particle contrast agents.

In one embodiment, the particle contrast agent 202 includes Safranin O. The Safranin O can be present in amounts sufficient to achieve between about 100 µM to about 1000 µM under staining conditions. The Safranin O can be present in amounts sufficient to achieve between about 600 µM to about 900 µM under staining conditions. The Safranin O can be present in amounts sufficient to achieve about 850 µM under staining conditions. The Safranin O can be present in amounts sufficient to achieve very nearly 850 µM under staining conditions. The Safranin O can be purified to at least 80% pure. The Safranin O can be purified to at least 81%, 82%, 83%, 84%, 85%, 86%, 87%, 88%, 89%, 90%, 91%, 92%, 93%, 94%, 95%, 96%, 97%, 98%, or 99% pure. The Safranin O can be purified to at least 100% pure.

In some embodiments, surprisingly effective results are achieved when the particle contrast agent 202 includes both Crystal Violet and Safranin O. The ratio of Crystal Violet to Safranin O can be between about 0.05:1 to about 5:1 (molar/molar). The ratio of Crystal Violet to Safranin O can be between about 3:1 (molar/molar). The ratio of Crystal Violet to Safranin O can be very nearly 3:1 (molar/molar).

In one embodiment, the particle contrast agent 202 includes New Methylene Blue. The New Methylene Blue can be purified to at least 50% pure. The New Methylene Blue can be purified to at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% pure. The New Methylene Blue can be purified to at least 100% pure.

In one embodiment, the particle contrast agent 202 includes Eosin Y. The Eosin Y can be purified to at least 80% pure. The Eosin Y can be purified to at least 81%, 82%, 83%, 84%, 85%, 86%, 87%, 88%, 89%, 90%, 91%, 92%, 93%, 94%, 95%, 96%, 97%, 98%, or 99% pure. The Eosin Y can be purified to at least 100% pure.

In one embodiment, the particle contrast agent 202 includes Methyl Green. The Methyl Green can be purified to at least 80% pure. The Methyl Green can be purified to at least 81%, 82%, 83%, 84%, 85%, 86%, 87%, 88%, 89%, 90%, 91%, 92%, 93%, 94%, 95%, 96%, 97%, 98%, or 99% pure. The Methyl Green can be purified to at least 100% pure.

In some embodiments, the particle contrast agent 202 includes one or more of Crystal Violet, New Methylene Blue, Safranin O, Eosin Y and Methyl Green in amounts effective to generate visual distinctions in particles, for example, by enhancing intracellular content features of particles in a sample when presented for imaging. The particle contrast agent 202 can be present in amounts sufficient to enhance and/or stain particles including erythrocytes (RBCs), dysmorphic erythrocytes, leukocytes (WBCs), neutrophils, lymphocytes, phagocytic cells, eosinophils, basophils, squamous epithelial cells, transitional epithelial cells, decoy cells, renal tubular epithelial cells, casts, crystals, bacteria, yeast, parasites, oval fat bodies, fat droplets, spermatozoa, mucus, *trichomonas*, cell clumps, cell fragments, and other cells found in urinary samples, as well as subcellular structures thereof. Staining can aid in identifying, distinguishing, counting, characterizing, and analyzing the particles, and/or identifying morphological features associated with pathologies, diseases, or conditions. Visualizable or visual distinctions can include any particle or intraparticle features that may be visualizable or otherwise detectable using any light source (e.g., UV, visible, IR).

In embodiments where the particle contrast agent composition 210 includes two or more particle contrast agents 202, the amounts of each of the particle contrast agents 202 can be adjusted appropriately, depending on whether the particle contrast agents 202 have independent, competitive and/or enhancing effects on the generation of visual distinctions for particle categorization and subcategorization.

Permeabilizing Agent

In some embodiments, the permeabilizing agent 204 can be a particle membrane and/or wall permeabilizing agent. The permeabilizing agent 204 can include a surfactant and/or a surface tension modifier. In some embodiments, the permeabilizing agent 204 can include a saponin. In alternate embodiments, the permeabilizing agent 204 can include at least one of a quarternary ammonium salt, a nonionic surfactant, and a zwitterionic surfactant. The permeabilizing agent can alter the permeability of a cell in order to increase accessibility of the particle contrast agent 202 to the intracellular contents. The permeabilizing agent can be selected and included in quantities sufficient to permit a rapid, one-step staining procedure.

Examples of a nonionic surfactant can include (1) polyoxyethylene alkyl or aryl ethers (polyethoxylates), including straight-chain aliphatic hydrophobes etherified to polyethylene glycol or polyoxyethylene ethanol, e.g., Brij® 35; (2) branched-chain aliphatic/aromatic (e.g., octylphenol) hydrophobes etherified to polyethylene glycol, e.g., Triton X®-100; (3) straight-chain aliphatic/aromatic (e.g., n-nonylphenol) hydrophobes etherified to polyethylene glycol, e.g., Igepal® C0897; and (4) straight-chain aliphatic (e.g., carboxylic acid) hydrophobes esterified to polyethylene glycol, e.g., Myrj® 53, and others. Examples of nonionic polyoxyethylene alkyl or aryl ethers (polyethoxylates) surfactants can include polyoxyethylene(4) lauryl ether (Brij® 30); polyoxyethylene(23) lauryl ether (Brij® 35); polyoxyethylene(2) cetyl ether (Brij® 52); polyoxyethylene(20) cetyl ether (Brij® 58); polyoxyethylene(2) stearyl ether (Brij® 72); polyoxyethylene(10)stearyl ether (Brij® 76); polyoxyethylene(20) stearyl ether (Brij® 78); polyoxyethylene(2) oleyl ether (Brij® 92); polyoxyethylene(10) oleyl ether (Brij® 96); polyoxyethylene(20) oleyl ether (Brij®

98); polyoxyethylene (21) stearyl ether (Brij® 721); polyoxyethylene(100) stearyl ether (Brij® 700); and others. Further examples of nonionic surfactants can include Triton X®-100 (non-reduced or reduced), Triton® X-114 non-reduced or reduced), Triton X®-165, and Triton X®-305 (non-reduced and reduced), and others.

In an embodiment, the permeabilizing agent 204 can include a nonionic surfactant (e.g., Brij® 35) at amounts sufficient to result in concentrations of about 0.10 g/L to about 0.20 g/L under staining conditions. The nonionic surfactant can be present in amounts sufficient to result in concentrations of about 0.10 g/L to about 0.16 g/L under staining conditions. The nonionic surfactant can be present in amounts sufficient to result in concentrations of about 0.012 g/L to about 0.14 g/L.

Examples of zwitterionic surfactants can include TDAPS (tetradecyldimethylammoniopropanesulfonate), CHAPSO (3-[(3-cholamidopropyl) dimethylammonio]-2-hydroxy-1-propanesulfonate), alkyl N, N-dimethyl N-oxides having from about 12 to about 16 carbon atoms, lauryl dimethylamine N-oxide (LO), DDAPS (N-dodecyl-N, N-dimethyl-3-ammonio-1-propanesulfonate), and others.

In some embodiments, the permeabilizing agent 204 includes an agent sufficient to increase the permeability of cells, membranes, and/or walls while leaving the cell structure substantially intact. In some embodiments, the permeabilizing agent 204 renders the membranes and/or walls more permeable and/or porous to facilitate access by the particle contrast agent 202.

In some embodiments, the permeabilizing agent 204 is selected to be able to quickly create the pores or openings necessary to allow the particle contrast agent 202 to enter cells in the sample.

Through non-trivial efforts and experimentation, it has been found that surprisingly effective results can be achieved in some embodiments of the particle contrast agent composition 210 with the use of a permeabilizing agent 204 that includes 5PD-Lytic available from Clinical Diagnostic Solutions (CDS) in Ft. Lauderdale, Fla. 5PD-Lytic includes saponin. 5PD-Lytic is generally described in U.S. Pat. No. 6,632,676, herein incorporated by reference. Surprisingly effective results can be achieved when using 5PD-Lytic at ratios of about 23.3% by weight of the particle contrast agent composition 210. Surprisingly effective results can be achieved when using 5PD-Lytic at ratios of very nearly 23.3% by weight of the particle contrast agent composition 210.

In some embodiments, a permeabilizing agent 204 includes a saponin present in amounts sufficient to result in concentrations of about 0.01 mg/L to about 100 mg/L under staining conditions. In some embodiments, the saponin is present in amounts sufficient to result in concentrations of about 0.05 mg/L to about 11 mg/L. In surprisingly effective embodiments, the saponin is present in amounts sufficient to result in concentrations of about 0.2 mg/L under staining conditions. In surprisingly effective embodiments, the saponin is present in amounts sufficient to result in concentrations of very nearly 0.2 mg/L under staining conditions. The concentration of the saponin stock solution before addition to the sample may be up to 100× the final saponin concentration. Since commercial saponin is not a pure material, adjustments in the concentration may be needed for various lots of saponin powder supplied. Within limits, it is possible to change the concentration of saponin added to a given urine sample, if a compensating change in volume of the saponin reagent is also made. In some embodiments, the saponin can be a quarternary ammonium-substituted saponin ether.

Fixing Agent

In some embodiments, the fixing agent 206 can be selected to ensure desired cells and cell structures do not degrade during staining and imaging. Examples of fixing agents can include glutaraldyde; formaldehyde; Diazolidinyl Urea; cross-linking agents; ammonia picrate in isotonic saline (e.g., for methylene blue staining); ethyl alcohol; methanol (e.g., at room temperature, −20° C. or −70° C.); Heidenhain's Susa—$HgCl_2$, NaCl Trichloroacetic acid, formalin; Bouin's—Picric acid, Formalin, acetic acid; Duboseq-Brazil—Bouins with 80% EtOH; Carnoy's—EtOH, Chloroform, acetic acid; Zenker's—$HgC_{12}$, $K_2CrO_7$, $NaSO_4.H_2O$; acetocarmine; Gatensby's—Chromic acid, Osmium tetroxide, NaCl; Baker's—Formalin, $CaCl_2$; Smith's—$K_2Cr_2O_7$, formalin, acetic acid; 1% methyl green, 1% acetic acid; Phenol, formalin, glycerol, Genetian violet; Schaudin—$HgCl_2$, EtOH, acetic acid; Champy's—Chromic acid, $K_2CrO_7$, $OsO_4$; Fleming's—Cromic acid, OsO4, acetic acid; Formol-Silver—Formaldehyde, $AgNO_3$; Streck's Tissue Fixative—Bronopol, Diazolidinyl urea, $ZnSO_4.7H_2O$, sodium citrate; 1% imidazolidnyl urea in PBS; Glyoxal: Glyofix, Prefer, Safefix, Histochoice; Glydant—Hydantoin; Dimethylol urea; Sodium hydroxymethylglycinate; Karnovsky's; Mecuric chloride (B-5); Hollande's; and others.

In some embodiments, the fixing agent 206 can be an oxidizing agent, a mercurial, a picrate, a hepes-glutamic acid buffer-mediated organic solvent protection effect (HOPE) fixative, or a water soluble preservative. Examples of oxidizing agents include Potassium dichromate, chromic acid, potassium permanganate, and others. Examples of mercurial include B-5, Zernker's fixative, and others. Examples of water-soluble preservatives include methyl paraben, propyl paraben, dimethylolurea, 2-pyridinethiol-1-oxide, sorbic acid, potassium sorbate, and others.

Through non-trivial efforts and experimentation, it has been found that surprisingly effective results can be achieved in some embodiments of the particle contrast agent composition 210 with the use of a fixing agent 206 that includes at least one of Gluteraldehyde, Formaldehyde, and Diazolidinyl Urea.

In some embodiments, surprisingly effective results can be achieved by using a fixing agent 206 that includes Gluteraldehyde at or below 0.1% by weight.

In some embodiments, surprisingly effective results can be achieved by using a fixing agent 206 that includes Diazolidinyl Urea at or around 216 mM.

Additional Components

In some embodiments, optional additional components 212 can be optionally combined at block 208 into the particle contrast agent composition 210. Examples of additional components 212 can include a pH adjusting agent, buffer components, a sugar, a sugar alcohol, an osmotic adjusting agent, a protein stabilizer, an antimicrobial agent, an ionic strength modifier, a surfactant, and a chelating agent, and others. In some embodiments, surprisingly effective results can be achieved when the particle contrast agent composition 210 includes a phosphate buffered saline. In some embodiments, the particle contrast agent composition 210 can include a pH adjusting agent to keep the pH at or around 3. In some embodiments, surprisingly effective results can be achieved when the particle contrast agent composition 210 includes a pH adjusting agent to keep the pH at or around that of the urine sample.

In some embodiments, the particle contrast agent composition 210 comprises one or more sugars and/or sugar alcohols, or other membrane stabilizers. Sugar and sugar alcohols in solution can help preserve cells/cell membranes. Examples of suitable sugars include Trehalose, Maltose, Sucrose, glycerol, maltulose, isomaltose, cellobiose, lactulose, gentiobulose, melibiose, mannobiose, palatinose, kojibiose, nigerose, sophorose, mannitol, sorbitol, xylitol, inositol, rhamnitol, fucitol, ribitol, threitol, erythritol, and glucitol. Specifically, the sugar Trehalose has been found to inhibit hemolysis by saponin. The particle contrast agent composition 210 can include Trehalose in amounts sufficient to result in concentrations between about 5 to about 200 mM under staining conditions. Trehalose can be included in amounts sufficient to result in concentrations between about 10 to about 100 mM under staining conditions. Trehalose can be included in amounts sufficient to result in concentrations of about 67.7 mM under staining conditions. Trehalose is both a protein and membrane stabilizer and can be used to maintain cell integrity in extreme conditions of drying, heating, freezing, and/or enzymatic tissue disaggregation.

In some embodiments, the particle contrast agent composition 210 comprises one or more protein stabilizers or other compatible solutes that counter the destabilizing effects of urea. Examples of suitable protein stabilizers include methylamine and amino acid protein stabilizers, TriMethylAmineN-Oxide (TMAO), Trimethylamine, glycerophosphoryl choline, betaine, glycine-betaine, pipercolate betaine, sarcosine, N-carbamoyl-L-glutamine-I-amide, N-acetylglutaminyl-glutamine amide, taurine, dimethyl taurine, hypotaurine, N-methyl taurine, thiotaurine, octopine, arginine, glycine, dimethyl glycine, N-trimethyl glycine, ecotoine, proline, proline-betaine, beta-alanine, glutamate, glutamate-betaine, N-acetyl-beta lysine, choline-o-sulfate, GABA, homarine, and dimethylsulfonoproprionate. In an embodiment, a compatible solute strategy can to increase the intensity of staining of cells in urine samples while stabilizing cellular proteins. Trimethylamine N-oxide (TMAO) can counteract protein solubilization (destabilization) by urea and Sodium chloride found in urine. The TMAO can balance the effects of protein destabilizers in the ratio of one part TMAO to two parts protein destabilizer. In some embodiments, the particle contrast agent composition 210 can include TMAO in amounts sufficient to result in concentrations between about 5 mM to about 200 mM under staining conditions.

In some embodiments, the particle contrast agent composition 210 can include a buffer for adjusting pH. The buffer can also include at least one of a suitable viscosity agent/modifier, a fixative, an ionic strength modifier, a surfactant, and a detergent.

In some embodiments, the particle contrast agent composition 210 can include a viscosity modifying agent. In some embodiments the viscosity modifying agent can be glycerol. The % glycerol can vary depending on the desired property of the particular sample and analyzer used. Examples of viscosity modifying agents can include PVP, natural hydrocolloids (and derivatives), such as carrageenan, locust bean gum, guar gum, and gelatin; sugars (and derivatives), such as dextrose, fructose; polydextrose; dextrans; polydextrans; saccharides; and polysaccharides; semi-synthetic hydrocolloids (and derivatives), such as Methylcellulose, Carboxymethylcellulose; Synthetic hydrocolloids (and derivatives), such as Carbopol®; and others.

Rapid, One-Step Staining Process

Figure 3:
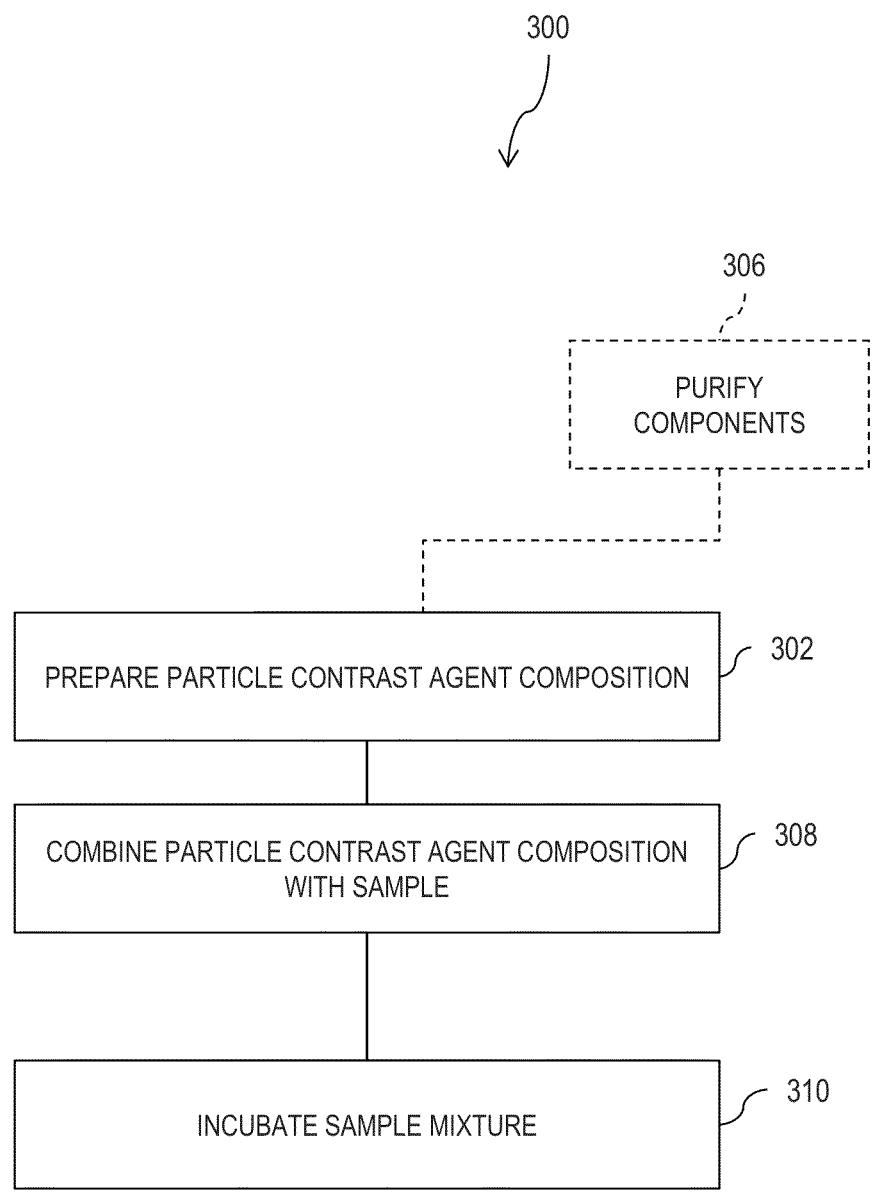
FIG. 3 is a flowchart of a rapid, one-step staining process according to one embodiment.

FIG. 3 is a flowchart of a rapid, one-step staining process 300 according to one embodiment. While the rapid, one-step staining process 300 can contain several sub-steps, the term "one-step" is used to identify that the sample need not be introduced to multiple, different solutions during the staining procedure. The particle contrast agent composition 210 is prepared at block 302, as described above with reference to FIG. 2. Optionally, in some embodiments, components, such as any particle contrast agents 202, can be purified at block 306. Purifying particle contrast agents 202 can reduce the level of precipitates formed upon contact with a sample, thereby reducing the background and improving the results of image-based urine sample analysis with a decreased need for further review of images or wet mounts, or manually prepared microscopy.

At block 308, the particle contrast agent composition 210 is combined with the sample. The particle contrast agent composition 210 can be combined with the sample in any suitable way, including mixing together. Combining at block 308 can include diluting the sample with a certain amount of particle contrast agent composition 210. The sample can be diluted with particle contrast agent composition 210. The amount of dilution can be selected to provide an optimal number of cells per frame during image-based analysis.

Through non-trivial efforts and experimentation, it has been found that surprisingly effective results can be achieved in some embodiments of the particle contrast agent composition 210 when combined with the sample up to 20% (v/v) particle contrast agent composition 210 in the resultant sample mixture. The percentage of particle contrast agent composition 210 in the resultant sample mixture can be about 1%, 2%, 3%, 4%, 5%, 6%, 7%, 8%, 9%, 10%, 11%, 12%, 13%, 14%, 15%, 16%, 17%, 18%, 19% or about 20% (v/v). Surprisingly effective results can be achieved by mixing the particle contrast agent composition 210 with the sample at a percentage of 15% particle contrast agent composition 210 (i.e., 85% sample) in the resultant sample mixture.

Through non-trivial efforts and experimentation, it has been found that surprisingly effective results can be achieved in some embodiments of the particle contrast agent composition 210 formulated to be mixed with a urine sample at a percentage at or below 15%. Staining with a low dilution can make an image-based urine sample analysis system very effective.

In some embodiments, the sample is combined with the particle contrast agent composition 210 at elevated temperatures, such as any of the temperatures described below with reference to incubating.

In certain embodiments, samples can be prepared or processed (e.g. concentrated, diluted) prior to combining with the particle contrast agent composition 210.

As used herein, the combined sample and particle contrast agent composition 210 is referred to as the sample mixture.

At block 310, the sample mixture is incubated for a certain amount of time at a certain temperature. Incubation can increase the permeability of the cells or their internal structures, allowing the particle contrast agent 202 to better infiltrate the cells or cellular structures. The time and temperature of incubation can be selected to enable the particle contrast agent composition 210 to properly permeate, fix, and stain the sample.

In an embodiment, the particle contrast agent composition 210 can include a surfactant and elevated heat during incubation can be used to achieve membrane permeabilization to retain RBC integrity and still achieve WBC, epithelial cells and bacteria staining efficacy at the desired resolution.

Through non-trivial efforts and experimentation, it has been found that surprisingly effective results can be achieved in some embodiments of the particle contrast agent composition 210 with incubation of the sample mixture at temperatures between about 40° C. and about 50° C. for about 1 to 90 seconds. The sample mixture can be heated to temperatures between about 41° C. and about 44° C. The sample mixture can be incubated for between 1 and 60 seconds. The sample mixture can be incubated for between 30 and 35 seconds. The sample mixture can be incubated for less than 30 seconds. In some embodiments, surprisingly effective results can be achieved by incubating the sample mixture between about 42° C. and about 43° C. for about 30 seconds.

In some embodiments, the combining at block 308 and the incubating at block 310 complete in approximately the same amount of time or less time than the time it takes for a sample mixture to be processed in the imaging equipment and for the lines of the imaging equipment to be flushed and/or cleaned. In this way, a first sample mixture can be imaged while a second sample mixture is being combined and incubated. Once the first sample mixture has been imaged and the imaging equipment has been cleaned, the second sample mixture can immediately be imaged.

In alternate embodiments, the combining at block 308 and the incubating at block 310 complete in less than twice the time it takes for a sample mixture to be processed in the imaging equipment and for the lines of the imaging equipment to be flushed and/or cleaned. In this way, while a first sample mixture is being imaged, a second sample mixture can be ready to be imaged, and a third sample mixture and fourth sample mixture can be in the process of being combined and incubated. Once the first sample mixture has been imaged and the imaging equipment has been cleaned, the second sample mixture can immediately be imaged. The third sample mixture can be finishing its combining and incubating and the fourth sample mixture can still be combining and incubating. Once the second sample mixture has been imaged and the imaging equipment has been cleaned, the third sample mixture can immediately be imaged, while the fourth sample mixture begins to finish combining and incubating and a fifth sample mixture begins combining and incubating. The process can continue indefinitely to continually image sample mixtures.

Through non-trivial efforts and experimentation, it has been found that surprisingly effective results can be achieved through a combination of certain embodiments of the particle contrast agent composition 210, certain ways of combining the particle contrast agent composition 210 with the sample, and certain ways of incubating the sample mixture.

Specifically, surprisingly effective results can be achieved by using a particle contrast agent composition 210 including 80% pure or greater Crystal Violet at about 0.57 mM under staining conditions, 23.3% by weight of 5PD-Lytic, and 0.05% of Proclin 300; where the particle contrast agent 210 is combined with the sample resulting in about 15% to about 20% concentration of the particle contrast agent composition by weight of the sample mixture; and where the resulting sample mixture is incubated at about 40° C. to about 50° C. for about 30 to 35 seconds.

Certain effective particle contrast agent compositions 210 and staining procedures enable rapid staining of samples with a relatively high urine to reagent ratio. Certain effective particle contrast agent compositions 210 and staining procedures enable rapid staining of samples such that various cellular components, nuclear lobes, and granular structures are clearly distinguishable. Certain effective particle contrast agent compositions 210 and staining procedures are suitable for supravital staining. Certain effective particle contrast agent compositions 210 and staining procedures are generate visual distinctions for particle categorization and subcategorization. Certain effective particle contrast agent compositions 210 and staining procedures are effective to enhance intracellular content features of particles in a serum, cerebrospinal fluid, pleural fluid, synovial fluid, seminal fluid, peritoneal fluid, amniotic fluid, lavage fluid, bone marrow aspirate fluid, effusions, exudates, or blood samples. Certain effective particle contrast agent compositions 210 and staining procedures are effective to stain neutrophils, lymphocytes, monocytes, eosinophils, basophils, platelets, reticulocytes, nucleated red blood cells, blasts, promyelocytes, myelocytes, metamyelocytes, casts, bacteria, epithelials, and/or parasites. Certain effective particle contrast agent compositions 210 and staining procedures are effective to generate visual distinctions for particle categorization and subcategorization, for example, by providing for differential staining of primary and secondary granules in cells, such as to aid in sub-categorization of immature granulocytes and their age determination based on the differential staining or enhancement of primary and secondary granules. Certain effective particle contrast agent compositions 210 and staining procedures are effective to generate visual distinctions for counting and characterizing white blood cells, epithelial cells and/or bacteria, including the categorization and sub categorization of white blood cells. Formed element identification can be facilitated. Certain effective particle contrast agent compositions 210 and staining procedures are effective to generate visual distinctions in vital and/or viable cells and/or cells with structures that remain substantially intact. Certain effective particle contrast agent compositions 210 and staining procedures are effective for staining bacteria, parasites, or *trichomonas*. Certain effective particle contrast agent compositions 210 and staining procedures are effective to identify, predict, diagnose, prognose, and/or support a diagnosis of a condition, disease, infection and/or syndrome and/or monitor whether a subject is responsive or non-responsive to treatment. Certain effective particle contrast agent compositions 210 and staining procedures are effective for staining of cells and/or cellular elements inclusions in urinary casts, which can be helpful for sub-categorization of casts.

The rapid staining enabled by certain effective particle contrast agent compositions 210 and staining procedures described herein can be used with manual or semi-automated imaging and/or analysis procedures.

Through non-trivial efforts and experimentation, it has been found that surprisingly effective results can be achieved when using a particle contrast agent composition 210 composed as listed in Table 1.

TABLE 1

| | |
|---|---|
| 0.150 mL | 1 mg/mL Crystal Violet dissolved in a lytic solution (e.g., CDS 5PD-Lytic) |
| 0.150 mL | Phosphate Buffered Saline, pH 7.2 |

Figure 4:
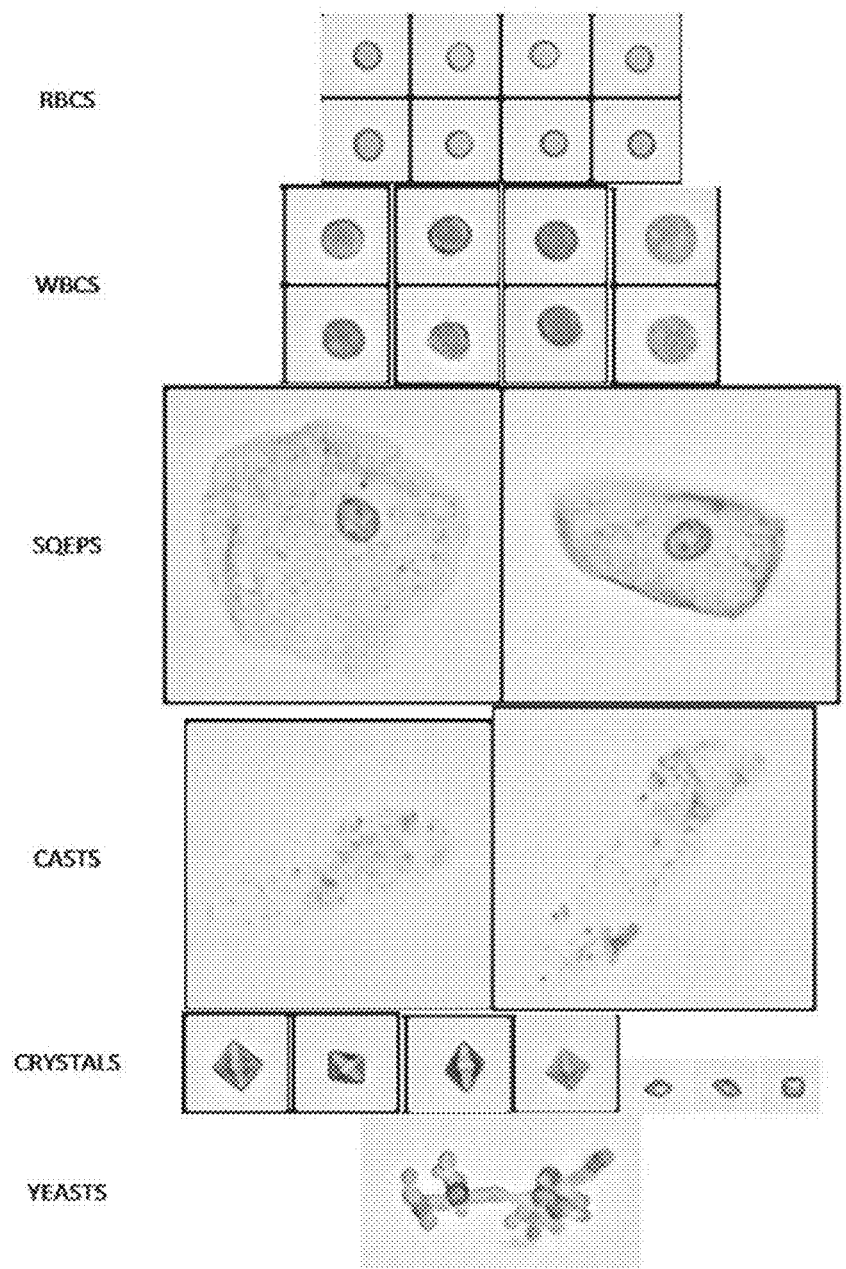
FIG. 4 is a representative illustration of selected particles from a urinary sample stained according to the rapid, one-step staining process according to one embodiment.

FIG. 4 is a representative illustration of selected particles from a urinary sample stained with the particle contrast agent composition 210 set forth in Table 1 and stained using the rapid, one-step staining procedures set forth above, specifically by pipetting 300 microL of the particle contrast agent composition 210 set forth in Table 1 into a test tube and mixing with 1.7 mL of urine sample, after which the sample mixture was warmed for 30 seconds in a water bath at 60° C. Red blood cells, white blood cells, squamous epithelial cells, casts, crystals, and yeasts are visually differentiable.

Through non-trivial efforts and experimentation, it has been found that surprisingly effective results can be achieved when using a particle contrast agent composition 210 composed as listed in Table 2.

TABLE 2

| 16 g | 1.07 mM | Tetronic 1107 |
|---|---|---|
| 25.6 g | 67.7 mM | Trehalose |
| 60 g | 216 mM | Diazolidinyl Urea |
| 0.792 g | 1.94 mM | Crystal Violet |
| 0.7920 g | 2.05 mM | Safranin O |
| 0.004 g | 0.0002 mM | Saponin |
| 5 mL | 15 ppm | Proclin 300 |
| 6 g | 54.5 mM | Diethylamine HCl (hygroscopic) |
| 1 g | 12.2 mM | Dimethylamine HCl (hygroscopic) |
| Add until 1 L | | Deionized Water |

Through non-trivial efforts and experimentation, it has been found that surprisingly effective results can be achieved when using a particle contrast agent composition 210 composed as listed in Table 3.

TABLE 3

| 0.57 mM | Crystal Violet |
|---|---|
| 76.7% (weight) | Deionized Water |
| 23.3% (weight) | 5 PD Lytic (CDS) |
| 0.05% (weight) | Proclin 300 |

Through non-trivial efforts and experimentation, it has been found that surprisingly effective results can be achieved when using a particle contrast agent composition 210 composed as listed in Table 4.

TABLE 4

| 0.57 mM | Crystal Violet |
|---|---|
| 76.7% (weight) | Deionized Water |
| 23.3% (weight) | 5 PD Lytic (CDS) |
| 0.05% (weight) | Proclin 300 |
| 119 mM | Sodium Chloride |
| 2.08 mM | Sodium Phosphate Dibasic |
| 1.18 mM | Potassium Phosphate Monobasic |

In some embodiments, features of imaged cells stained by the particle contrast agent compositions of this disclosure are noted in Table 5.

TABLE 5

| | Size (relative to RBC) | Shape | Color | Details |
|---|---|---|---|---|
| RBC | Standard | Round | | Light Center |
| WBC | Large | Round | Nucleus Stained | Nucleus & Granules |
| Epithelials | Small to large | Various | Nucleus Stained | Nucleus & Granules |
| Crystals | Small to large | Various | Natural | Corners |
| Bacteria | Very small and large rods | Dots or rods | Stained | |
| Yeast | Very small to large | Single round or clumps | | |

TABLE 5-continued

| | Size (relative to RBC) | Shape | Color | Details |
|---|---|---|---|---|
| Sperm | Small | Filaments | | Head and tail |
| Casts | Large to very large | Cylindroid | | Transparent |
| Mucus | Small to very large | Filaments or cylindroid | | Transparent |
| Trichomonas | Large | Round | Stained | Tail |

In certain embodiments, the particle contrast agent composition 210 is formulated for stability, ease of storage, disposal, and/or limited toxicity.

Early Experimentation

As described with reference to the examples below, numerous staining compositions and methods were tested and modified in order to result in the embodiments disclosed above.

Figure 5:
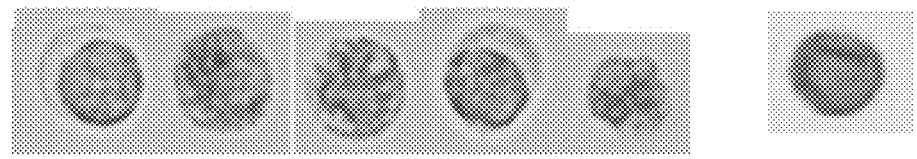
FIG. 5 is an image of selected particles from a urinary sample stained according to one early example.

In an early Example 1, a particle contrast agent composition included 0.1% Crystal Violet at 67 μM, 5PD-Lytic at 3.5%, and a Phosopate Buffered Saline with $NaPO_4$ at 332 μM and $KPO_4$ at 188 μM. The particle contrast agent composition was mixed with a 2.55 mL sample of urine. The results, as seen in FIG. 5, were too light and were ineffective for properly differentiating particles and cells. To improve the staining, Example 2 was attempted.

Figure 6:
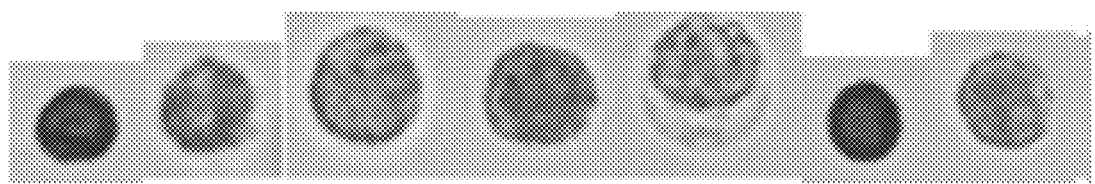
FIG. 6 is an image of selected particles from a urinary sample stained according to one early example.

In a subsequent Example 2, a particle contrast agent composition included Crystal Violet at 86 μM, 5PD-Lytic at 3.5%, and a Phosopate Buffered Saline with $NaPO_4$ at 312 μM and $KPO_4$ at 177 μM. The particle contrast agent composition was mixed with a 2.55 mL sample of urine. The results, as seen in FIG. 6, were ineffective for properly differentiating particles and cells. To improve the staining, Example 3 was attempted.

Figure 7:
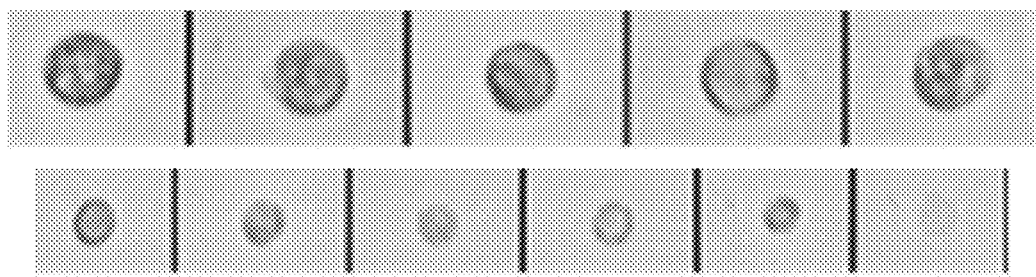
FIG. 7 is an image of selected particles from a urinary sample stained according to one early example.

In a subsequent Example 3, a particle contrast agent composition included a Crystal Violet Stain, deionized water, and additional diluent mixed with the urine sample at respective concentrations of 86 μM, 13.5% and 1%. The particle contrast agent composition was mixed with a 1.7 mL sample of urine. The results, as seen in FIG. 7, were very lightly stained and were ineffective for properly differentiating particles and cells. To improve the staining, Example 4 was attempted.

Figure 8:
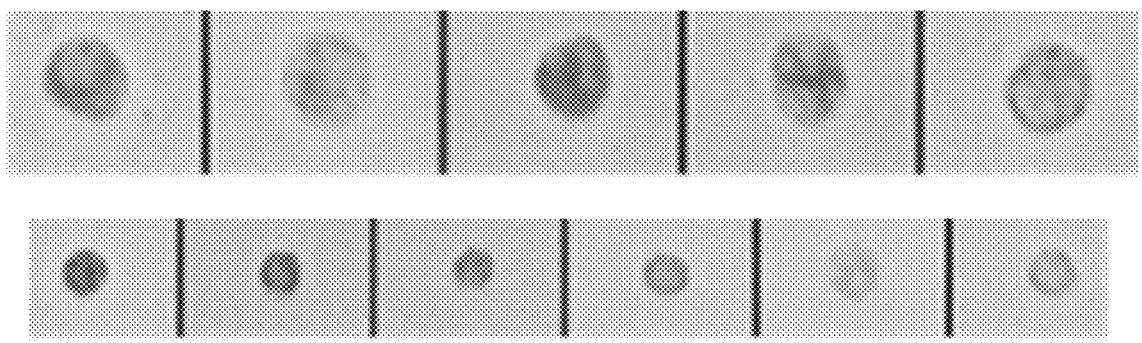
FIG. 8 is an image of selected particles from a urinary sample stained according to one early example.

In a subsequent Example 4, a particle contrast agent composition included a Crystal Violet Stain and deionized water mixed with the urine sample at respective concentrations of 86 μM and 13.5%. The particle contrast agent composition was mixed with a 1.7 mL sample of urine. The results, as seen in FIG. 8, displayed pale staining and were ineffective for properly differentiating particles and cells. To improve the staining, Example 5 was attempted.

Figure 9:
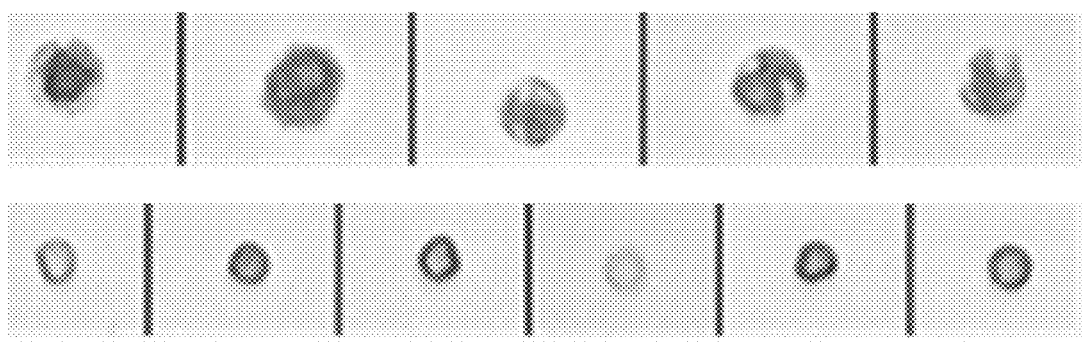
FIG. 9 is an image of selected particles from a urinary sample stained according to one early example.
Figure 10:
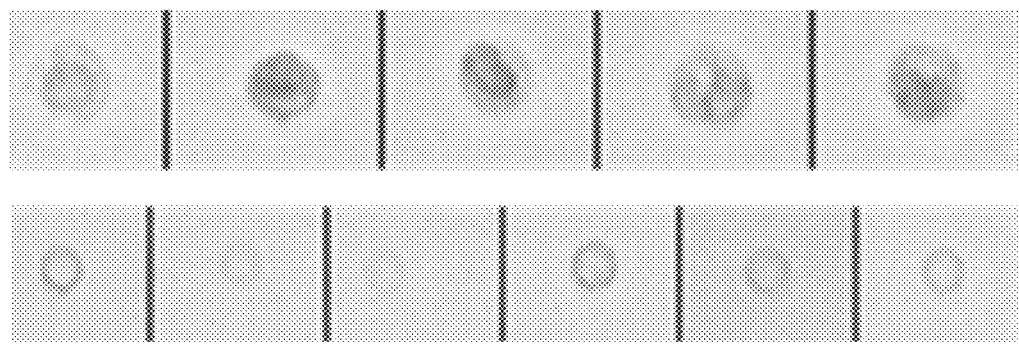
FIG. 10 is an image of selected particles from a urinary sample stained according to one early example.

In a subsequent Example 5, a particle contrast agent composition included Crystal Violet at 150 μM, 5PD-Lytic at 3.5%, Deionized Water at 30.6%, and Saponin at 0.0037 mg/mL. The particle contrast agent composition was mixed with a 1.7 mL sample of urine. The results, as seen in FIG. 9, contained overstained mucous and were ineffective for properly differentiating particles and cells. To improve the staining, Example 6 was attempted.

In a subsequent Example 6, a particle contrast agent composition included Crystal Violet at 52 μM, 5PD-Lytic at 3.5%, Deionized Water at 11.3%, and Saponin at 0.0075 mg/mL. The particle contrast agent composition was mixed with a 1.7 mL sample of urine. The results, as seen in FIG.

10, were too light and were ineffective for properly differentiating particles and cells. To improve the staining, Example 7 was attempted.

Figure 11:
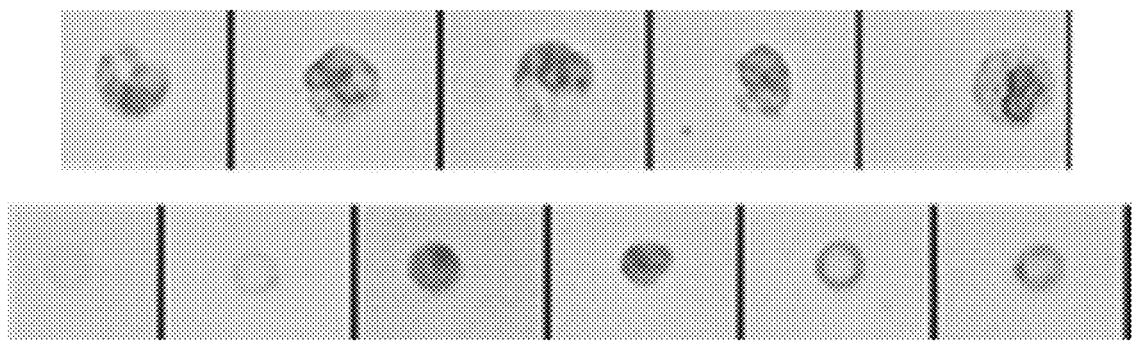
FIG. 11 is an image of selected particles from a urinary sample stained according to one early example.

In a subsequent Example 7, a particle contrast agent composition included Crystal Violet at 100 μM, 5PD-Lytic at 3.5%, Deionized Water at 9.4%, and Saponin at 0.0075 mg/mL. The particle contrast agent composition was mixed with a 1.7 mL sample of urine. The results, as seen in FIG. 11, were too light and were ineffective for properly differentiating particles and cells. To improve the staining, Example 8 was attempted.

Figure 12:
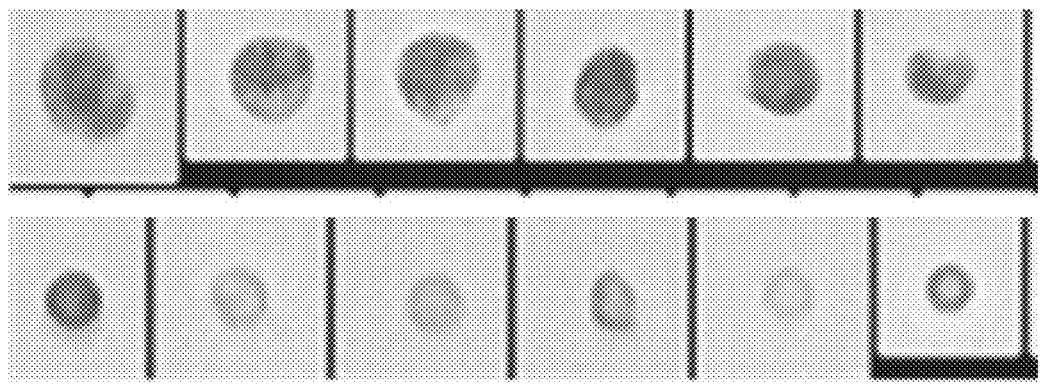
FIG. 12 is an image of selected particles from a urinary sample stained according to one early example.

In a subsequent Example 8, a particle contrast agent composition included Crystal Violet at 91 μM, 5PD-Lytic at 3.5%, and a Phosopate Buffered Saline with NaPO$_4$ at 203 μM and KPO$_4$ at 115 μM. The particle contrast agent composition was mixed with a 1.7 mL sample of urine. The results, as seen in FIG. 12, contained overstained mucous and were ineffective for properly differentiating particles and cells. To improve the staining, Example 9 was attempted.

Figure 13:
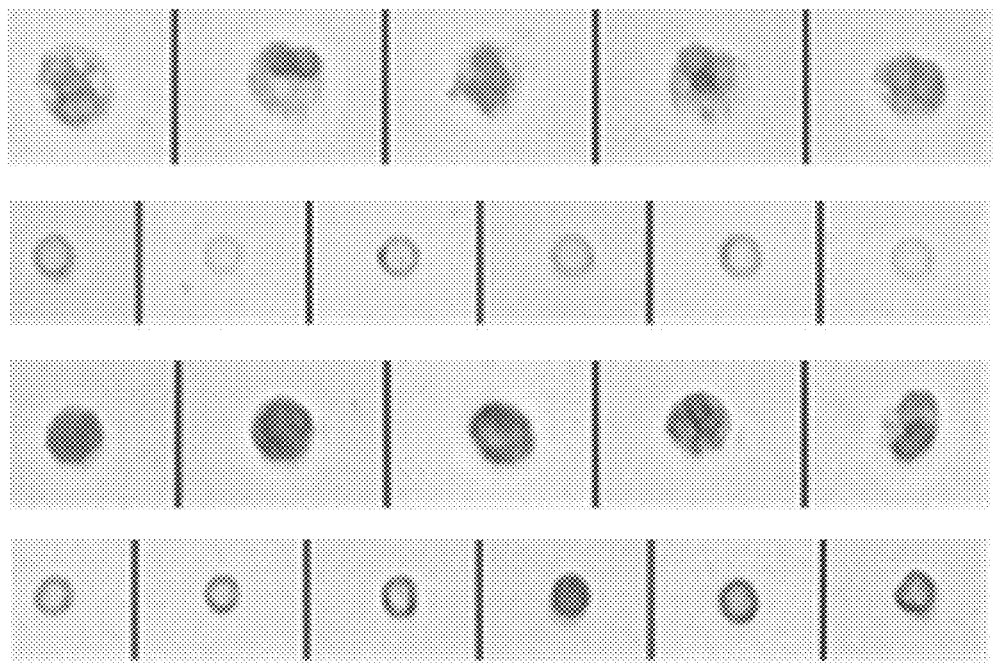
FIG. 13 is an image of selected particles from a urinary sample stained according to one early example.

In a subsequent Example 9, a particle contrast agent composition included Crystal Violet at 150 μM, 5PD-Lytic at 3.5%, Deionized Water at 7.3%, and Saponin at 0.0075 mg/mL. The particle contrast agent composition was mixed with a 1.7 mL sample of urine. The results, as seen in FIG. 13, contained overstained mucous and were ineffective for properly differentiating particles and cells. To improve the staining, Example 10 was attempted.

Figure 14:
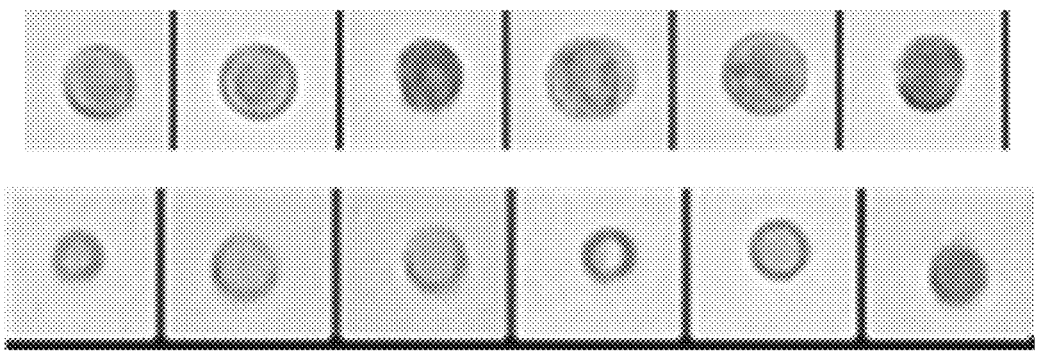
FIG. 14 is an image of selected particles from a urinary sample stained according to one early example.

In a subsequent Example 10, a particle contrast agent composition included Crystal Violet at 150 μM, 5PD-Lytic at 3.5%, and Deionized Water at 8.8%. The particle contrast agent composition was mixed with a 1.7 mL sample of urine. The results, as seen in FIG. 14, contained uneven staining and were ineffective for properly differentiating particles and cells. To improve the staining, Example 11 was attempted.

Figure 15:
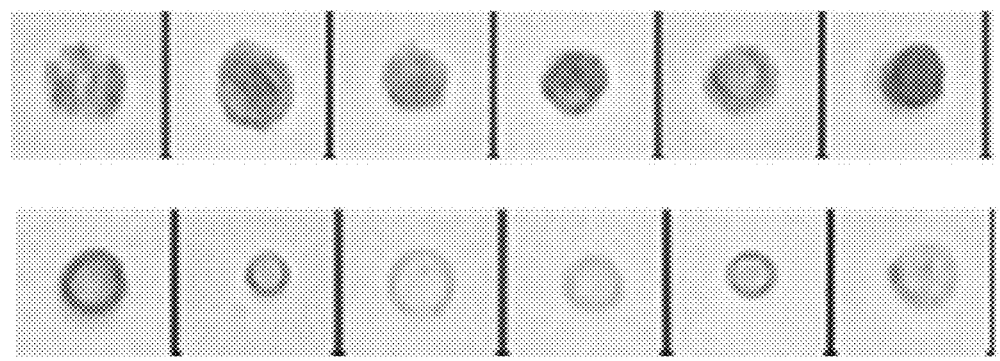
FIG. 15 is an image of selected particles from a urinary sample stained according to one early example.

In a subsequent Example 11, a particle contrast agent composition included Crystal Violet at 150 μM, 5PD-Lytic at 3.5%, Deionized Water at 8.8%, Saponin at 0.0075 mg/mL, and Gluteraldehyde at 0.03%. The particle contrast agent composition was mixed with a 1.7 mL sample of urine. The results, as seen in FIG. 15, contained overstained mucous and were ineffective for properly differentiating particles and cells. To improve the staining, Example 12 was attempted.

Figure 16:
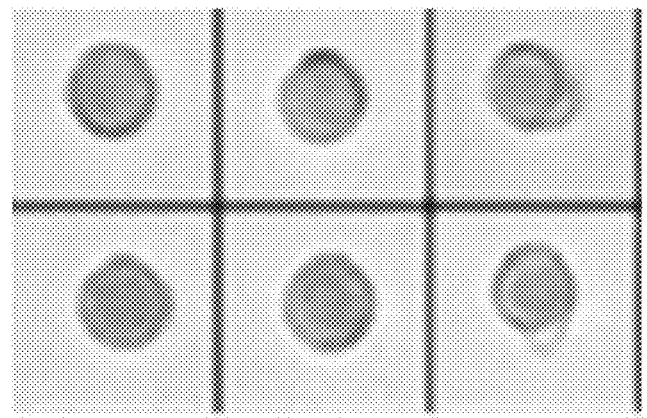
FIG. 16 is an image of selected particles from a urinary sample stained according to one early example.
Figure 16:
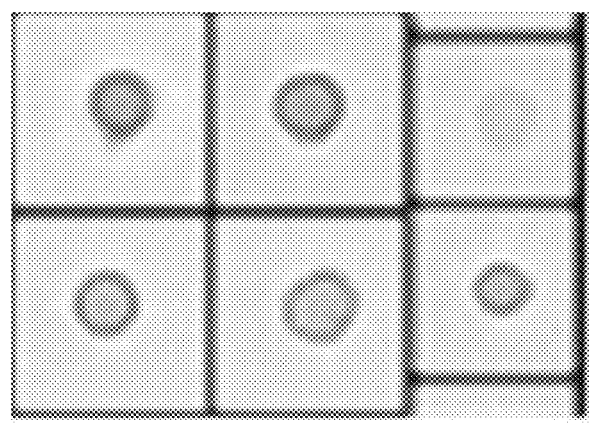

In a subsequent Example 12, a particle contrast agent composition included Crystal Violet at 86 μM, 50% Erythrolyze (made by Beckman Coulter) at 3.5%, and a Phosopate Buffered Saline with NaPO$_4$ at 312 μM and KPO$_4$ at 177 μM. The particle contrast agent composition was mixed with a 1.7 mL sample of urine. The results, as seen in FIG. 16, were ineffective for properly differentiating particles and cells. To improve the staining, Example 13 was attempted.

Figure 17:
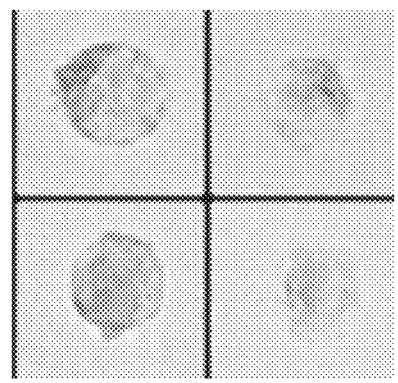
FIG. 17 is an image of selected particles from a urinary sample stained according to one early example.
Figure 17:
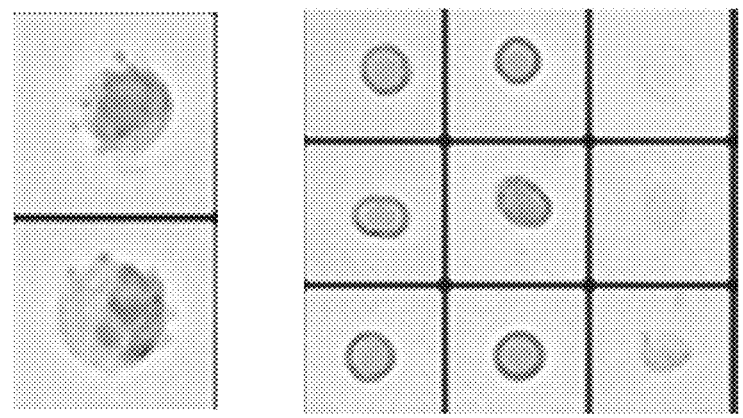

In a subsequent Example 13, a particle contrast agent composition included Crystal Violet at 285 μM, 5PD-Lytic at 3.5%, and a Phosopate Buffered Saline with NaPO$_4$ at 1040 μM and KPO$_4$ at 590 μM. The particle contrast agent composition was mixed with a 1.0 mL sample of urine. The results, as seen in FIG. 17, were ineffective for properly differentiating particles and cells. To improve the staining, Example 14 was attempted.

Figure 18:
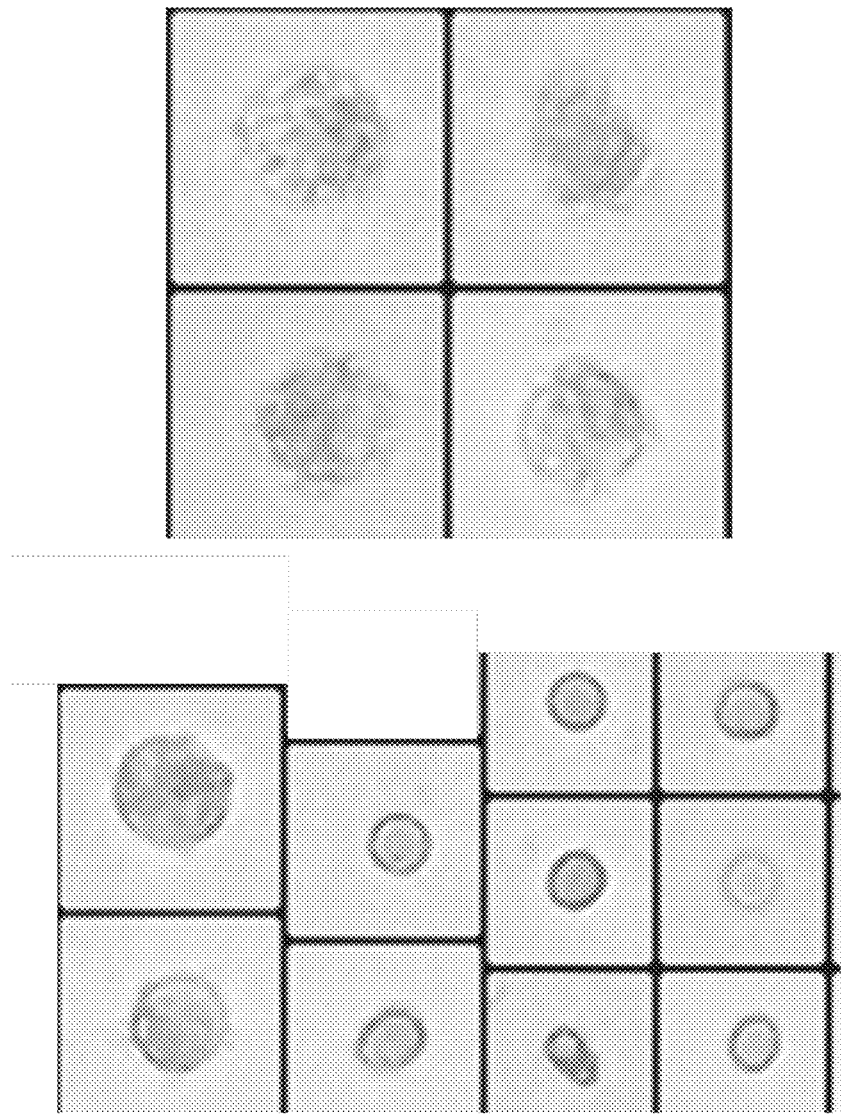
FIG. 18 is an image of selected particles from a urinary sample stained according to one early example.

In a subsequent Example 14, a particle contrast agent composition included Crystal Violet at 28 μM, 5PD-Lytic at 3.5%, and a Phosopate Buffered Saline with NaPO$_4$ at 104 μM and KPO$_4$ at 0.059 μM. The particle contrast agent composition was mixed with a 1.9 mL sample of urine. The results, as seen in FIG. 18, were ineffective for properly differentiating particles and cells. To improve the staining, Example 15 was attempted.

Figure 19:
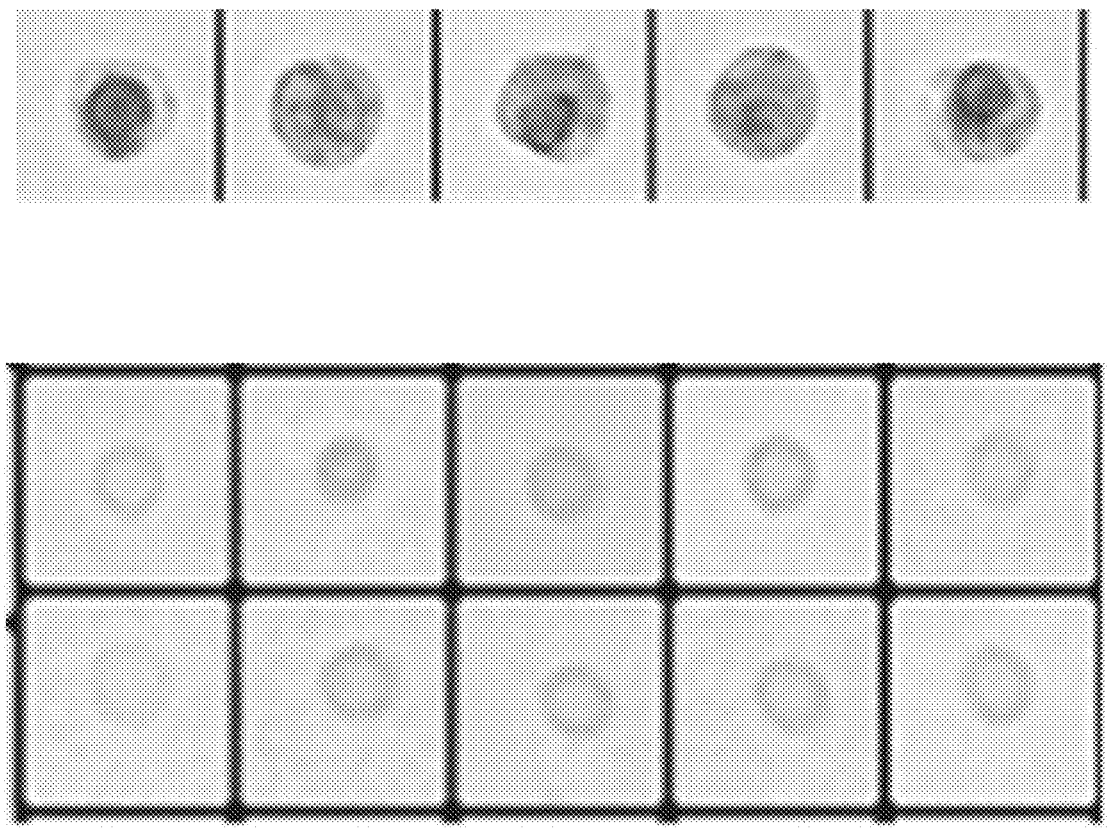
FIG. 19 is an image of selected particles from a urinary sample stained according to one early example.

In a subsequent Example 15, a particle contrast agent composition included Crystal Violet at 91 μM, Sapponin/Potassium Pyrosulfate solution at 3.5%, and no Phosopate Buffered Saline. The particle contrast agent composition was mixed with a 1.850 mL sample of urine. The results, as seen in FIG. 19, contained overstained mucous resulted in ineffective staining. To improve the staining, Example 16 was attempted.

Figure 20:
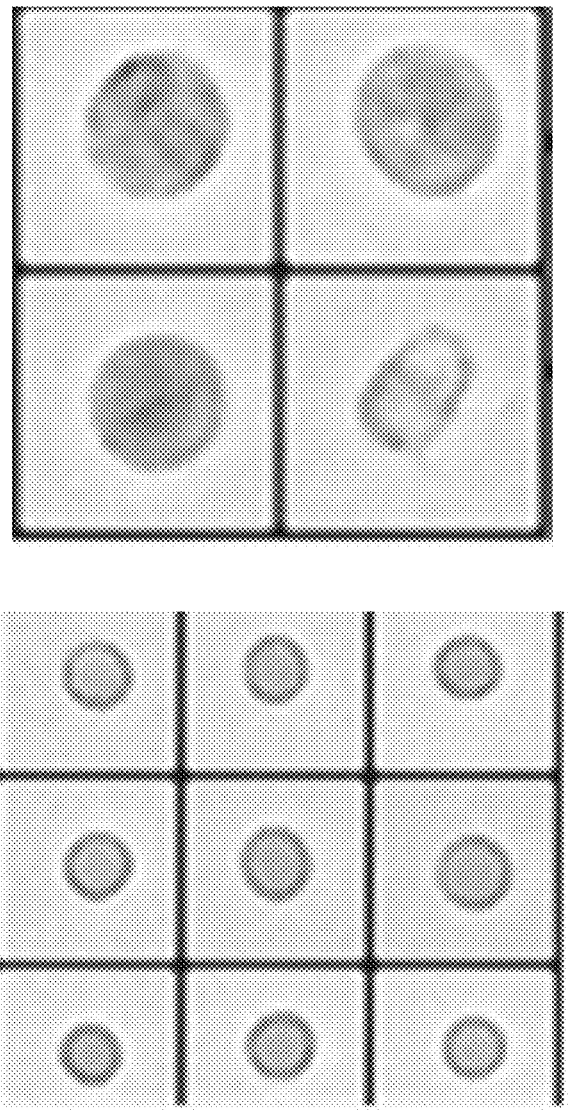
FIG. 20 is an image of selected particles from a urinary sample stained according to one early example.

In a subsequent Example 16, a particle contrast agent composition included Crystal Violet at 86 μM, 50% Erythrolyze (made by Beckman Coulter) at 3.5%, and a Phosopate Buffered Saline with NaPO$_4$ at 312 μM and KPO$_4$ at 177 μM. The particle contrast agent composition was mixed with a 1.7 mL sample of urine. The results, as seen in FIG. 20, are not stained with sufficient darkness and clarity. To improve the staining, Example 17 was attempted.

Figure 21:
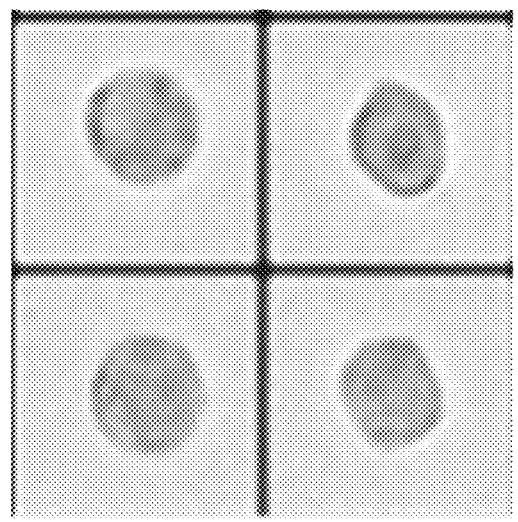
FIG. 21 is an image of selected particles from a urinary sample stained according to one early example.
Figure 21:
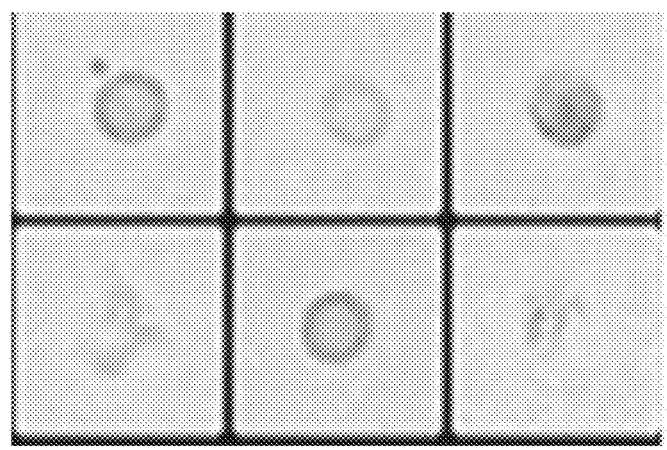

In a subsequent Example 17, a particle contrast agent composition included Crystal Violet at 86 μM, Sapponin/Potassium Pyrosulfate solution at 3.5%, and a Phosopate Buffered Saline with NaPO$_4$ at 312 μM and KPO$_4$ at 177 μM. The particle contrast agent composition was mixed with a 1.7 mL sample of urine. The results, as seen in FIG. 21, are not stained with sufficient darkness and clarity. To improve the staining, additional embodiments of the particle contrast agent composition as disclosed herein were attempted.

In numerous early examples, the particle contrast agent concentration included many variations of Trehalose (TRE), Trimethyl Amine N-oxide (TMAO), Tetronic 1107 (T1107), Tetronic 90R4 (T90R4), Crystal Violet (CV), Safranine O (SO), Saponin (SAP), Diethyl Amine chloride (DEA), Dimethyl Amine chloride (DMA), and Diazonlidinyl Urea (DU), as described in Table 6, below.

TABLE 6

| Example | TRE mM | TMAO mM | T1107 mg/mL | T90R4 mg/mL | CV μM | SO μM | SAP mg/L | DEA % | DMA % | DU mg/mL |
|---|---|---|---|---|---|---|---|---|---|---|
| 18 | 10 | 84 | 0.02 | 0 | 60 | 0 | 0.05 | 0 | 0 | 0 |
| 19 | 10 | 84 | 0.02 | 0 | 90 | 0 | 0.05 | 0 | 0 | 0 |
| 20 | 40 | 84 | 0.02 | 0 | 90 | 0 | 0.05 | 0 | 0 | 0 |
| 21 | 10 | 84 | 0.08 | 0 | 90 | 0 | 0.05 | 0 | 0 | 0 |
| 22 | 10 | 330 | 0.02 | 0 | 90 | 0 | 0.05 | 0 | 0 | 0 |
| 23 | 10 | 84 | 0.08 | 0 | 90 | 0 | 0.05 | 0 | 0 | 0 |
| 24 | 10 | 84 | 0 | 0 | 60 | 0 | 0.05 | 0 | 0 | 0 |
| 25 | 15 | 126 | 0.03 | 0 | 60 | 0 | 0.05 | 0 | 0 | 0 |
| 26 | 10 | 84 | 0.02 | 0 | 60 | 0 | 0.05 | 0 | 0 | 0 |
| 27 | 10 | 84 | 0.02 | 0 | 60 | 0 | 0.05 | 0 | 0 | 0 |
| 28 | 10 | 84 | 0.02 | 0 | 60 | 0 | 0.05 | 0 | 0 | 0 |
| 29 | 40 | 84 | 0.02 | 0 | 60 | 0 | 0.05 | 0 | 0 | 0 |
| 30 | 10 | 330 | 0.02 | 0 | 60 | 0 | 0.05 | 0 | 0 | 0 |

TABLE 6-continued

| Example | TRE mM | TMAO mM | T1107 mg/mL | T90R4 mg/mL | CV μM | SO μM | SAP mg/L | DEA % | DMA % | DU mg/mL |
|---|---|---|---|---|---|---|---|---|---|---|
| 31 | 10 | 84 | 0.08 | 0 | 60 | 0 | 0.05 | 0 | 0 | 0 |
| 32 | 10 | 84 | 0.02 | 0 | 60 | 0 | 0.05 | 0 | 0 | 0 |
| 33 | 10 | 84 | 0.02 | 0 | 60 | 580 | 0.05 | 0 | 0 | 0 |
| 34 | 10 | 84 | 0.2 | 0 | 60 | 870 | 0.05 | 0 | 0 | 0 |
| 35 | 50 | 84 | 0.2 | 0 | 60 | 0 | 0.05 | 0 | 0 | 0 |
| 36 | 50 | 84 | 0.2 | 0 | 60 | 1160 | 0.05 | 0 | 0 | 0 |
| 37 | 10 | 84 | 0.8 | 0 | 60 | 1160 | 0.05 | 0 | 0 | 0 |
| 38 | 10 | 84 | 0.8 | 0 | 60 | 0 | 0.05 | 0 | 0 | 0 |
| 39 | 10 | 84 | 1 | 0 | 120 | 580 | 0.005 | 0 | 0 | 0 |
| 40 | 10 | 84 | 1 | 0 | 120 | 580 | 0.003 | 0 | 0 | 0 |
| 41 | 10 | 84 | 4 | 0 | 120 | 580 | 0.05 | 0 | 0 | 0 |
| 42 | 10 | 84 | 1 | 0 | 120 | 580 | 0.05 | 0 | 0 | 0 |
| 43 | 40 | 84 | 1 | 0 | 120 | 580 | 0.05 | 0 | 0 | 0 |
| 44 | 10 | 336 | 1 | 0 | 120 | 580 | 0.05 | 0 | 0 | 0 |
| 45 | 10 | 84 | 4 | 0 | 120 | 580 | 0.05 | 0 | 0 | 0 |
| 46 | 10.6 | 264 | 2 | 0 | 128 | 570 | 0.05 | 0 | 0 | 0 |
| 47 | 10.6 | 528 | 0.2 | 0 | 128 | 570 | 0.05 | 0 | 0 | 0 |
| 48 | 10.6 | 84 | 0 | 0 | 120 | 580 | 2 | 0 | 0 | 0 |
| 49 | 10.6 | 84 | 4 | 0 | 334 | 854 | 2 | 0 | 0 | 0 |
| 50 | 10.6 | 84 | 4 | 0 | 250 | 1139 | 0.2 | 0 | 0 | 0 |
| 51 | 10.6 | 84 | 4 | 0 | 300 | 100 | 0.1 | 0 | 0 | 0 |
| 52 | 10.6 | 252 | 4 | 0 | 300 | 100 | 0.1 | 0 | 0 | 0 |
| 53 | 10.6 | 168 | 4 | 0 | 300 | 100 | 0.1 | 0 | 0 | 0 |
| 54 | 10.6 | 168 | 4 | 0 | 350 | 100 | 0.1 | 0 | 0 | 0 |
| 55 | 10.6 | 168 | 4 | 0 | 400 | 100 | 0.1 | 0 | 0 | 0 |
| 56 | 10.6 | 151 | 4 | 0 | 350 | 100 | 0.1 | 0 | 0 | 0 |
| 57 | 6.8 | 45 | 1.6 | 0 | 419 | 100 | 0.2 | 0 | 0 | 0 |
| 58 | 6.8 | 0 | 1.6 | 0 | 419 | 100 | 0.2 | 0 | 0 | 0 |
| 59 | 6.8 | 45 | 0 | 0 | 419 | 100 | 0.2 | 0 | 0 | 0 |
| 60 | 0 | 45 | 1.6 | 0 | 419 | 100 | 0.2 | 0 | 0 | 0 |
| 61 | 6.8 | 45 | 1.6 | 0 | 0 | 100 | 0.2 | 0 | 0 | 0 |
| 62 | 6.8 | 45 | 1.6 | 0 | 419 | 0 | 0.2 | 0 | 0 | 0 |
| 63 | 6.8 | 45 | 1.6 | 0 | 419 | 100 | 0 | 0 | 0 | 0 |
| 64 | 6.8 | 0 | 1.6 | 0 | 419 | 100 | 0.2 | 0 | 0 | 0 |
| 65 | 6.8 | 0 | 1.6 | 0 | 308 | 100 | 0.2 | 0 | 0 | 0 |
| 66 | 6.8 | 0 | 1.6 | 0 | 167 | 100 | 0.2 | 0 | 0 | 0 |
| 67 | 6.8 | 0 | 1.6 | 0 | 167 | 100 | 0.2 | 0 | 0 | 3 |
| 68 | 6.8 | 0 | 1.6 | 0 | 200 | 100 | 0.4 | 0 | 0 | 6 |
| 69 | 6.8 | 0 | 1.6 | 0 | 250 | 100 | 0.4 | 0 | 0 | 6 |
| 70 | 6.8 | 0 | 1.6 | 0 | 300 | 100 | 0.6 | 0 | 0 | 3 |
| 71 | 6.8 | 0 | 1.6 | 0 | 300 | 200 | 0.6 | 0 | 0 | 3 |
| 72 | 6.8 | 0 | 1.6 | 0 | 300 | 200 | 0.6 | 0.6 | 0.1 | 3 |
| 73 | 6.8 | 0 | 1.6 | 0 | 200 | 200 | 0.4 | 0.6 | 0.1 | 6 |
| 74 | 6.8 | 0 | 1.6 | 0 | 300 | 100 | 0.6 | 0.6 | 0.1 | 3 |
| 75 | 6.8 | 0 | 1.6 | 0 | 350 | 100 | 0.2 | 0.6 | 0.1 | 3 |
| 76 | 13.6 | 0 | 3.2 | 1 | 400 | 100 | 0 | 0.6 | 0.15 | 6 |

Examples 18-76 did not provide optimal results for distinguishing cells.

All patents, patent publications, patent applications, journal articles, books, technical references, and the like discussed in the instant disclosure are incorporated herein by reference in their entirety for all purposes.

Any headers used herein are for organizational purposes only and are not to be construed to limit the disclosure or claims in any way.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. In certain cases, method steps or operations may be performed or executed in differing order, or operations may be added, deleted or modified. It can be appreciated that, in certain aspects of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention. Accordingly, the present invention is not limited to the embodiments described above or depicted in the drawings, and various embodiments and modifications can be made without departing from the scope of the claims below.

What is claimed is:

1. A particle contrast agent composition for staining particles of a urological fluid sample for imaging in an automated particle analysis system comprising:
    a particle contrast agent selected from the group consisting of Crystal Violet, New Methylene Blue, Safranin O, Eosin Y, and Methyl Green;
    a permeabilizing agent including a 5-part differential (5 PD) lytic reagent including saponin, wherein the saponin is present in amounts sufficient to result in concentrations of about 0.01 mg/L to about 100 mg/L under staining conditions; and
    an antimicrobial agent.

2. The composition of claim 1, wherein the particle contrast agent includes Safranin O present in amounts sufficient to result in concentrations of between about 100 µM to about 1000 µM under staining conditions.

3. The composition of claim 1, wherein the particle contrast agent further includes Crystal Violet and Safranin O, and wherein the molar-to-molar ratio of the Crystal Violet to the Safranin O is between about 0.05:1 to about 5:1.

4. The composition of claim 1, wherein:
the 5-PD lytic reagent is present in amounts sufficient to result in concentrations of about 3.5% by weight under staining conditions.

5. The composition of claim 1, additionally comprising:
a phosphate buffered saline including at least sodium phosphate dibasic and potassium phosphate monobasic.

6. The composition of claim 1, additionally including:
sodium chloride; and
a phosphate buffered saline including at least sodium phosphate dibasic and potassium phosphate monobasic.

7. The composition of claim 1, further comprising a fixing agent.

8. The composition of claim 7, wherein the fixing agent is selected from the group consisting of gluteraldehyde, formaldehyde, and diazolidinyl urea.

9. The composition of claim 1, wherein the particle contrast agent comprises Crystal Violet.

10. The composition of claim 1, wherein the particle contrast agent comprises New Methylene Blue.

11. The composition of claim 1, wherein the particle contrast agent comprises Eosin Y.

12. The composition of claim 1, wherein the particle contrast agent comprises Methyl Green.

13. A method of treating particles of a urological fluid sample for imaging using in an automated particle analysis system comprising:
combining a particle contrast agent composition and the urological fluid sample into a sample mixture resulting in a final concentration of the particle contrast agent composition by weight of the sample mixture between about 1% and about 20%; and
incubating the sample mixture at a temperature above 20° Celsius for fewer than 90 seconds;
wherein the particle contrast agent composition comprises:
a particle contrast agent selected from the group consisting of Crystal Violet, New Methylene Blue, Safranin O, Eosin Y, and Methyl Green;
a permeabilizing agent including a 5-part differential (5 PD) lytic reagent including saponin, wherein the saponin is present in amounts sufficient to result in concentrations of about 0.01 mg/L to about 100 mg/L under staining conditions, and
an antimicrobial agent.

14. The method of claim 13, wherein the particle contrast agent includes Safranin O present in amounts sufficient to result in concentrations of between about 100 µM to about 1000 µM under staining conditions.

15. The method of claim 13, wherein the particle contrast agent includes Crystal Violet and Safranin O, and wherein the molar-to-molar ratio of the Crystal Violet to the Safranin O is between about 0.05:1 to about 5:1.

16. The method of claim 13, wherein:
the 5 PD Lytic reagent is present in amounts sufficient to result in concentrations of about 3.5% by weight under staining conditions; and
the final concentration of particle contrast agent composition by weight of the sample mixture is between about 10% and about 20%; and
the incubating the sample mixture includes incubating the sample mixture between 30° C. and 50° C. for fewer than 60 seconds.

17. The method of claim 13, wherein
the final concentration of particle contrast agent composition by weight of the sample mixture is about 15%; and
the incubating the sample mixture includes incubating the sample mixture between 30° C. and 50° C. for fewer than 60 seconds.

18. The method of claim 13, wherein:
the incubating the sample mixture includes incubating the sample mixture between 40° C. and 50° C. for between 30 and 35 seconds.

19. The method of claim 13, wherein:
the particle contrast agent composition further comprises sodium chloride and a phosphate buffered saline including at least sodium phosphate dibasic and potassium phosphate monobasic.

20. The method of claim 13, wherein the particle contrast agent composition further comprises a fixing agent.

\* \* \* \* \*